US012667823B2

(12) United States Patent
Zaworotko et al.

(10) Patent No.: US 12,667,823 B2
(45) Date of Patent: Jun. 30, 2026

(54) RELATING TO GAS SEPARATION

(71) Applicant: UNIVERSITY OF LIMERICK, Limerick (IE)

(72) Inventors: Michael John Zaworotko, Limerick (IE); Kai-Jie Chen, Limerick (IE); David G Madden, Limerick (IE); Soumya Mukherjee, Limerick (IE); Amrit Kumar, Limerick (IE)

(73) Assignee: University of Limerick, Limerick (IE)

( * ) Notice: Subject to any disclaimer, the term of this patent is extended or adjusted under 35 U.S.C. 154(b) by 365 days.

(21) Appl. No.: 17/753,705

(22) PCT Filed: Sep. 13, 2020

(86) PCT No.: PCT/EP2020/075584
§ 371 (c)(1),
(2) Date: Mar. 11, 2022

(87) PCT Pub. No.: WO2021/048432
PCT Pub. Date: Mar. 18, 2021

(65) Prior Publication Data

US 2022/0355268 A1 Nov. 10, 2022

(30) Foreign Application Priority Data

Sep. 13, 2019 (EP) .................................... 19197407

(51) Int. Cl.
*B01D 53/02* (2006.01)
*B01J 20/22* (2006.01)
(Continued)

(52) U.S. Cl.
CPC ............ *B01J 20/226* (2013.01); *B01D 53/02* (2013.01); *B01J 20/2808* (2013.01);
(Continued)

(58) Field of Classification Search
CPC ............... B01J 20/226; B01J 20/28057; B01J 20/2808; B01J 20/3458; B01J 20/3483;
(Continued)

(56) References Cited

U.S. PATENT DOCUMENTS 4,874,525 A * 10/1989 Markovs ............ B01D 53/0423 95/134
6,432,171 B1 * 8/2002 Kumar ................... B01D 53/02 95/902
(Continued)

FOREIGN PATENT DOCUMENTS

CN 109651055 A 4/2019
EP 2746248 A1 6/2014
(Continued)

OTHER PUBLICATIONS

Liao et al. ("Efficient purification of ethene by an ethane-trapping metal-organic framework." Nature communications 6.1 (2015): 8697) (Year: 2015).*
(Continued)

*Primary Examiner* — In Suk C Bullock
*Assistant Examiner* — Jason Y Chong
(74) *Attorney, Agent, or Firm* — Hoffman Warnick LLC

(57) ABSTRACT

A method of purifying gaseous mixtures, for example ternary or quaternary gaseous mixtures, using a sorbent media comprising two or more sorbent materials. The method involves obtaining a target gas from a gaseous composition comprising the target gas, a first gas and a second gas, and optionally further gases by contacting the gaseous composition with the sorbent media to remove at least some of the first gas and at least some of the second gas from the gaseous composition. The sorbent media comprises at least a first sorbent material and a second sorbent material; wherein the first sorbent material has a higher adsorption selectivity for
(Continued)

the first gas than for the target gas; and wherein the second sorbent material has a higher adsorption selectivity for the second gas than for target gas. The method may be particularly useful for the separation of pure ethylene, methane or propylene from such gaseous mixtures. A sorbent media and an apparatus for obtaining a target gas from such a gaseous composition are also disclosed.

13 Claims, 23 Drawing Sheets

(51) Int. Cl.

*B01J 20/28* (2006.01)
*B01J 20/34* (2006.01)
*C07C 7/12* (2006.01)

(52) U.S. Cl.

CPC ....... *B01J 20/3458* (2013.01); *B01J 20/3483* (2013.01); *C07C 7/12* (2013.01); *B01D 2253/204* (2013.01); *B01D 2256/24* (2013.01); *B01D 2256/245* (2013.01); *B01D 2257/504* (2013.01); *B01D 2257/7022* (2013.01); *B01D 2257/7025* (2013.01); *B01D 2259/4143* (2013.01)

(58) Field of Classification Search

CPC .............. B01D 53/02; B01D 2253/204; B01D 2256/22; B01D 2256/24; B01D 2256/245; B01D 2257/504; B01D 2257/7022; B01D 2257/7025; B01D 2259/401; B01D 2259/402; B01D 2259/403; B01D 2259/414; B01D 2259/4143; B01D 2259/4145; C07C 7/12; C10L 2290/542; C10L 3/101; C10L 3/104; Y02C 20/40; Y02P 20/151; Y02P 20/156; Y02P 20/20; Y02P 20/50

See application file for complete search history.

(56) References Cited

U.S. PATENT DOCUMENTS

| | | | | |
|---|---|---|---|---|
| 2018/0155258 | A1 | 6/2018 | Lavenn et al. | |
| 2019/0054413 | A1 * | 2/2019 | Xing | B01D 53/02 |

FOREIGN PATENT DOCUMENTS

| | | | | | |
|---|---|---|---|---|---|
| FR | 3005873 | A1 | | 11/2014 | |
| JP | 2001129342 | A | | 5/2001 | |
| KR | 20200120029 | A | * | 10/2020 | B01J 20/20 |
| WO | 2013159797 | A1 | | 10/2013 | |
| WO | 2016018437 | A1 | | 2/2016 | |
| WO | 2017132816 | A1 | | 8/2017 | |
| WO | 2018118105 | A1 | | 6/2018 | |

OTHER PUBLICATIONS

PCT International Search Report and Written Opinion for International Application No. PCT/EP2020/075584, dated Jun. 29, 2021, 26 pages.

European Search Report for Application No. EP19197407, dated May 27, 2020, 8 pages.

Stephen Burd, "Porous Metal-Organic Materials by Design Using Neutral Organic Ligands," University of South Florida, Scholar Commons, Apr. 1, 2011, 39 pages.

Li et al., "Metal-organic frameworks based upon non-zeotype 4-connected topolgy," Coordination Chemistry Reviews, 2014, 27 pages.

Gandara et al., "Porous, Conductive Metal-Triazolates and Their Structural Elucidation by the Charge-Flipping Method," Chemistry, A European Journal, 2012, 18, 10595-10601.

George M. Sheldrick, "A short history of SHELX," Acta Crystallographica, Section A, 2008, A64, 112-122.

Zhang et al., "Temperature and Concentration Control over Interpenetration in a Metal-Organic Material," American Chemical Society, 2009, 2 pages.

Zhang et al., "Template-directed synthesis of metal-organic materials," The Royal Society of Chemistry, Chem. Soc. Rev., 2014, 43, 5444-5455.

Kai-Ji Chen et al., "New Zn-Aminotriazolate-Dicarboxylate Frameworks: Synthesis, Structures and Adsorption Properties," American Chemical Society, Cryst. Growth Des., 2013, 13, 2118-2123.

Blessing, "An Empirical Correction for Absorption Anisotropy," Acta Cryst., 1995, A51, 33-38.

Barbour, "X-Seed—A Software Tool for Supramolecular Crystallography," Journal of Supramolecular Chemistry, 2001, 1, 189-191.

* cited by examiner

RELATING TO GAS SEPARATION

The present invention relates to a method of obtaining a target gas from a gaseous composition comprising the target gas and at least two other gases. The present invention also relates to the use of a sorbent material for obtaining the target gas from such a gaseous composition and to an apparatus for carrying out said methods and uses. In particular, the present invention relates to energy efficient methods of purifying hydrocarbons such as ethylene, propylene and methane.

At present, purification of commodities consumes about 15% of global energy. Commodities include agricultural products, fuels and metals and the demand for such commodities has been projected to triple by 2050. For example, ethylene and propylene are some of the world's most important chemicals—the production of ethylene ($C_2H_4$) and propylene ($C_3H_6$) alone accounts for 0.3% of global energy use. Over 60% of raw ethylene is used in the plastics industry, with industrial uses of ethylene including polymerisation to form poly(ethylene) amongst others.

Polymerisation-grade (defined as being above 99.9% purity) ethylene is produced by a separation of downstream $C_2$ hydrocarbon gas mixtures produced by a steam cracking process. Such gas mixtures comprise hydrocarbons, notably other $C_2$ hydrocarbons such as acetylene ($C_2H_2$) and ethane ($C_2H_6$), as well as trace impurities such as carbon dioxide ($CO_2$). Acetylene is removed from such gas mixtures either via catalytic hydrogenation or solvent extraction. Catalytic hydrogenation involves the use of a metal catalyst at high temperatures and pressures, while solvent extraction requires a significant solvent volume and a large operating unit. Ethane is typically removed using cryogenic distillation. However, all of the aforementioned methods involve high energy consumption and costly processes. There is therefore a need to develop less energy-intensive methods of obtaining high purity ethylene from gas mixtures comprising other hydrocarbon gases and impurities.

Therefore to obtain polymer-grade ethylene in a one-step process it is necessary to remove both acetylene and ethane, and any other trace impurities, from an impure ethylene gas. In principle, this could be achieved in several ways, for example using chemical transformation, chemisorption, extraction or membrane-based technologies. However, all of these approaches have drawbacks. For example, the methods may make use of expensive raw materials, require specialist equipment or take significant amount of time. In any case, it has not yet proven to be possible to carry out such a purification of ethylene in one-step using these methods.

The use of physisorbents for the purification of gaseous hydrocarbons such as ethylene could significantly improve the efficiency of their production. Physisorbents are able to physically bond to gas molecules due to the presence of weak, long range van der Waals interactions. Known physisorbents typically comprise cavities or pores to facilitate such adsorption and examples include zeolites and porous metal-organic frameworks. However, it does not appear to be possible to simultaneously remove acetylene, ethane and other trace impurities from ethylene using a known physisorbent material, due to the similarity in size and chemistry of $C_2$ hydrocarbon molecules, which limits the selectivity of most physisorbents for each of acetylene, ethane and other trace impurities over ethylene. This is further complicated when trace impurities such as carbon dioxide are present as the physisorbent would need a strong affinity towards acetylene, ethane and carbon dioxide over ethylene.

It is an aim of the present invention to provide a method, use or apparatus that addresses at least one disadvantage of the prior art, whether identified here or elsewhere, or to provide an alternative to existing methods, uses or apparatus. For instance, it is an aim of embodiments of the present invention to provide a method of obtaining ethylene from a gaseous composition comprising ethylene and at least two other gases.

According to example embodiments, there is provided a method, use and apparatus as set forth in the appended claims. Other features of the invention will be apparent from the dependent claims, and the description which follows.

According to a first aspect of the present invention, there is provided a method of obtaining a target gas from a gaseous composition comprising the target gas, a first gas and a second gas, the method comprising the step of contacting the gaseous composition with a sorbent media to remove at least some of the first gas and at least some of the second gas from the gaseous composition; wherein the sorbent media comprises a first sorbent material and a second sorbent material; wherein the first sorbent material has a higher adsorption selectivity for the first gas than for the target gas; and wherein the second sorbent material has a higher adsorption selectivity for the second gas than for the target gas.

The method of this first aspect may be considered to be a method of increasing the concentration of a target gas in the gaseous composition comprising the target gas, the first gas and the second gas, the method comprising contacting the gaseous composition with the sorbent media. The method involves increasing the concentration of the target gas in the (starting) gaseous composition, by removal of at least some of the first gas and the second gas, suitably substantially all of the first gas and the second gas.

The first and second gases are different to each other and are not the same as the target gas. Therefore the gaseous composition comprises the target gas and at least two different other gases. The first and second gases may be considered to be impurity gases. Therefore the first gas may be referred to as a first impurity gas and the second gas may be referred to as a second impurity gas. The gaseous composition comprising the target gas may therefore be considered to be an impure gaseous composition and the method of this first aspect may be considered to produce a target gas with an increased purity. The method of this first aspect may therefore be considered to be a method of purifying a target gas.

The target gas is suitably ethylene, propylene, propane or methane.

The sorbent media is suitably a solid sorbent media, suitably a solid material which is stable to allow mechanical handling. Suitably the sorbent media is provided as a bed, for example on a suitable support material/structure. The sorbent media comprises a first sorbent material and a second sorbent material. The first and second sorbent materials are different to each other, but may be structurally related or from what is considered to be the same class of sorbent materials. For example, the first and/or the second sorbent material may be solid microporous sorbent materials, suitably hybrid porous materials or hybrid ultramicroporous materials (HUMs). Such sorbent materials may be alternatively defined as metal organic materials (MOMs), metal organic frameworks (MOFs) or porous coordination polymers (PCPs). The sorbent materials may be known as physisorbent materials.

The sorbent media may comprise the first and second sorbent materials, and any further sorbent materials, in discrete sections, for example discrete sections arranged in series on a bed wherein the gaseous composition contacts the first sorbent material as it passes over or through the sorbent media and then contacts the second sorbent media, or vice versa. In some embodiments, the sorbent media may comprise the first and second sorbent materials, and any further sorbent materials, in a mixture, for example wherein the first and second sorbent materials are randomly distributed throughout the sorbent media. In such embodiments, the gaseous composition would contact both the first and second sorbent materials at the same time and throughout the passing of the gaseous mixture over or through the sorbent media. Suitably the sorbent media may comprise the first and second sorbent materials, and any further sorbent materials, in discrete sections arranged in series. The inventors have found that the method of obtaining a target gas from a gaseous composition comprising the target gas can be more efficient if the different sorbent materials are in discrete sections arranged in series, rather than being mixed.

The contacting of gaseous composition with a sorbent media to remove at least some of the first gas and at least some of the second gas from the gaseous composition is carried in one step or operation, for example in a single chamber through which the gaseous composition is passed in the method. The contacting of the gaseous composition with the first sorbent material in the sorbent media is carried out at the same time and/or within the same step or operation as the contacting of the gaseous composition with the second sorbent material in the sorbent media, rather than during separate steps or operations or in separate chambers.

In the method of this first aspect, the first sorbent material selectively adsorbs the first gas and the second sorbent material selectively adsorbs the second gas. Therefore, at least two separate gas adsorption processes are occurring in the method when the gaseous composition contacts the sorbent media.

By appropriate selection of the first and second sorbent materials, the inventors have found that a target gas, for example ethylene, can be advantageously obtained or purified from a gaseous composition containing the target gas and at least two other different gases, for example acetylene, ethane and/or carbon dioxide, in a single operation in the method of this first aspect by contacting the gaseous composition with the sorbent media to remove the first and second gases. The target gas may be obtained in greater purity than known methods wherein a single sorbent material is used. For example, ethylene may be obtained in a more cost effective and/or energy efficient manner compared to the known, multi-step methods of purifying ethylene discussed above.

According to a second aspect of the present invention, there is provided a use of a sorbent media comprising a first sorbent material and a second sorbent material, to increase the concentration of a target gas in a gaseous composition comprising the target gas, a first gas and a second gas; wherein the sorbent media selectively adsorbs the first gas and the second gas over the target gas.

Figure 1:
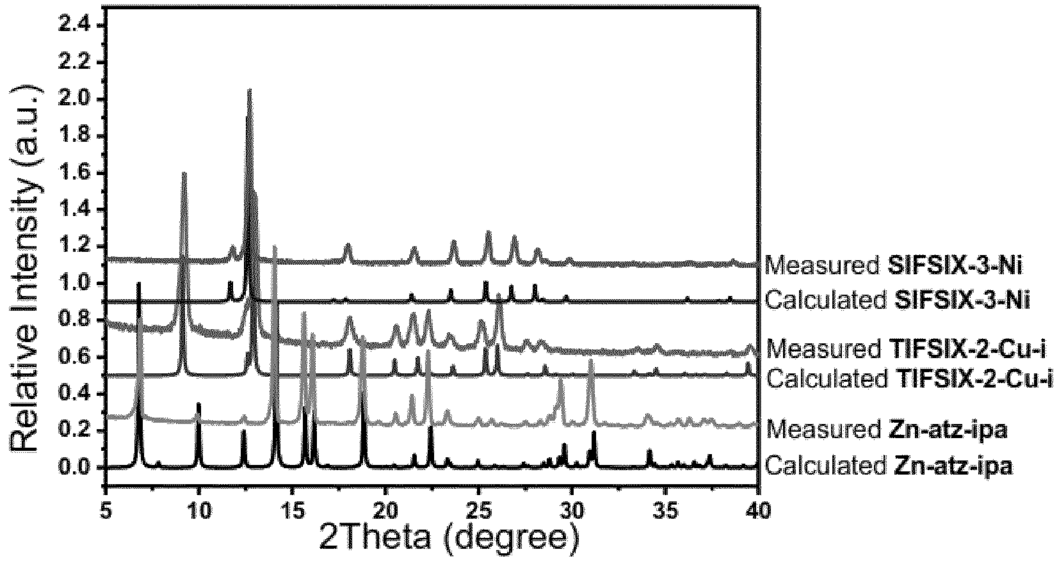
FIG. 1: Measured and calculated powder X-ray diffraction patterns of TIFSIX-2-Cu-i, SIFSIX-3-Ni and Zn-atz-ipa.

Preferred features of the first and second aspects of the invention will now be described.

The gaseous composition comprises a target gas. Suitably the target gas is a hydrocarbon, such as a hydrocarbon which is typically contaminated with $C_2$ hydrocarbons after production and requires purification by removal of said $C_2$ hydrocarbons. The target gas is suitably a $C_{1-4}$ hydrocarbon. The present invention may be particularly effective in the purification of ethylene, propylene, propane and methane. The target gas may be selected from ethylene, propylene, propane and methane. The present invention may be particularly effective in the purification of ethylene and methane. The target gas may be selected from ethylene and methane.

The gaseous composition comprising a target gas, a first gas and a second gas is suitably obtained from a petrochemical process. Suitably the gaseous composition comprises hydrocarbons, suitably $C_2$ hydrocarbons. Suitably the gaseous composition comprises ethylene ($C_2H_4$) and other $C_2$ hydrocarbons, for example acetylene ($C_2H_2$) and ethane ($C_2H_6$). The gaseous composition may comprise trace gases, for example carbon dioxide ($CO_2$), carbon monoxide (CO) and water ($H_2O$).

Suitably the first gas is acetylene. Suitably the second gas is ethane. Suitably the first gas is acetylene and the second gas is ethane.

In some embodiments, the target gas is ethylene. In such embodiments, the gaseous composition suitably comprises ethylene, acetylene and ethane. The gaseous composition may comprise a third gas, suitably carbon dioxide. In such embodiments the gaseous composition may comprise ethylene, acetylene, ethane and carbon dioxide. The gaseous composition is suitably a composition produced industrially from which ethylene is currently extracted by known methods.

In some embodiments, the gaseous mixture is a ternary gaseous mixture, suitably consisting essentially of or consisting of ethylene, acetylene and ethane. In some embodiments, the gaseous mixture is a quaternary gaseous mixture, suitably consisting essentially of or consisting of ethylene, acetylene, ethane and carbon dioxide.

Suitably the gaseous composition comprises at least 20 wt % ethylene, suitably at least 25 wt %, for example at least 30 wt % ethylene.

Suitably the gaseous composition comprises up to 90 wt % ethylene, suitably up to 80 wt %, for example up to 75 wt % ethylene.

Suitably the gaseous composition comprises from 20 to 90 wt % ethylene, suitably from 25 to 80 wt %, for example from 30 to 75 wt % ethylene.

Suitably the gaseous composition comprises at least 0.001 wt % acetylene, suitably at least 0.01 wt %, for example at least 0.1 wt % acetylene.

Suitably the gaseous composition comprises up to 5 wt % acetylene, suitably up to 2 wt %, for example up to 1.5 wt % acetylene.

Suitably the gaseous composition comprises from 0.001 to 5 wt % acetylene, suitably from 0.01 to 4 wt %, suitably from 0.05 to 3 wt % suitably from 0.1 to 2 wt %, for example from 0.5 to 1.5 wt % acetylene.

Suitably the gaseous composition comprises at least 20 wt % ethane, suitably at least 25 wt %, for example at least 30 wt % ethane.

Suitably the gaseous composition comprises up to 70 wt % ethane, suitably up to 65 wt %, for example up to 60 wt % ethane.

Suitably the gaseous composition comprises from 20 to 70 wt % ethane, suitably from 25 to 65 wt %, for example from 30 to 60 wt % ethane.

Suitably the gaseous mixture comprises from 30 to 75 wt % ethylene, from 0.1 to 2 wt % acetylene and from 30 to 60 wt % ethane.

In embodiments wherein the gaseous mixture comprises carbon dioxide, the gaseous composition suitably comprises at least 5 wt % carbon dioxide, suitably at least 10 wt %, for example at least 20 wt % carbon dioxide.

The gaseous composition suitably comprises up to 60 wt % carbon dioxide, suitably up to 50 wt %, for example up to 40 wt % carbon dioxide.

The gaseous composition suitably comprises from 10 to 60 wt % carbon dioxide, suitably from 15 to 50 wt %, for example from 20 to 40 wt % carbon dioxide.

Suitably the gaseous mixture comprises from 25 to 75 wt % ethylene, from 0.1 to 2 wt % acetylene, from 25 to 60 wt % ethane and from 15 to 50 wt % carbon dioxide.

In some embodiments, the target gas is methane. In such embodiments, the gaseous composition suitably comprises methane, acetylene and ethane. The gaseous composition may comprise a third gas, suitably carbon dioxide. In such embodiments the gaseous composition may comprise methane, acetylene, ethane and carbon dioxide. The gaseous composition is suitably a composition produced industrially from which methane is currently extracted by known methods.

In such embodiments, the gaseous mixture may be a ternary gaseous mixture, suitably consisting essentially of or consisting of methane, acetylene and ethane. In such embodiments, the gaseous mixture may be a quaternary gaseous mixture, suitably consisting essentially of or consisting of methane, acetylene, ethane and carbon dioxide.

In such embodiments, the methane may be present in the gaseous composition in the amounts described above for ethylene. The acetylene, ethane and carbon dioxide, when present, may be present in the amounts described above.

The method and use of the present invention involves contacting the gaseous composition with the sorbent media. This suitably involves passing the gaseous composition through a chamber comprising the sorbent media, suitably wherein the sorbent media is provided as a fixed bed. Contacting the gaseous composition with the sorbent media allows at least a part of the first gas and the second gas, and any third or further gases present, to be adsorbed onto and/or into the sorbent materials which make up the sorbent media. Suitably the first and second gases are adsorbed onto an inner surface of the first and second sorbent materials, respectively, suitably an inner surface of the pores of the sorbent materials. This removes at least some of (and suitably substantially all of) the first gas and the second gas, and any third or further gases present, from the gaseous composition, leaving an increased concentration of ethylene in the gaseous composition after contact with the sorbent media compared with before contact with the sorbent media.

The sorbent media comprises the first sorbent material and the second sorbent material. The first sorbent material has a higher adsorption selectivity for the first gas than for the target gas. Suitably the first sorbent material has a higher adsorption selectivity for the first gas than for the target gas and the second gas, and suitably also for any third or further gas present. The first gas is suitably acetylene and therefore the first sorbent material suitably has a higher adsorption selectivity for acetylene than for the target gas, suitably ethylene or methane. The first sorbent material suitably has a higher adsorption selectivity for acetylene than for the target gas and ethane. The first sorbent material suitably has a higher adsorption selectivity for acetylene than for the target gas, ethane and carbon dioxide.

The second sorbent material has a higher adsorption selectivity for the second gas than for the target gas. Suitably the second sorbent material has a higher adsorption selectivity for the second gas than for the target gas and the first gas, and suitably also for any third or further gas present. The second gas is suitably ethane and therefore the second sorbent material suitably has a higher adsorption selectivity for ethane than for the target gas, suitably ethylene and methane. The second sorbent material suitably has a higher adsorption selectivity for ethane than for the target gas and acetylene. The second sorbent material suitably has a higher adsorption selectivity for ethane than for the target gas, acetylene and carbon dioxide.

Suitably the first and second sorbent materials, and any third or further sorbent materials present, may be selected from ultramicroporous materials such as hybrid ultramicroporous materials (HUMs). Suitable ultramicroporous materials comprise a three-dimensional lattice of metal species (M) and linker groups. Suitably the metal species (M) are linked together in a first and second dimension by first linker groups ($L^1$) and are linked together in a third dimension by second linker groups ($L^2$) to form the three-dimensional lattice.

The First Sorbent Material

The first sorbent material is suitably an ultramicroporous material wherein one of $L^1$ and $L^2$ is an organic linker group and the other of $L^1$ and $L^2$ is an inorganic linker group, which has a higher adsorption selectivity for acetylene than for ethylene and ethane, and suitably carbon dioxide.

Suitably the first sorbent material has the chemical formula: $M(L^1)_2(L^2)$, which may additionally comprise anions such as halogen ions, where appropriate. Therefore the first sorbent may have the formula $M_x(L^1)_2(L^2)Y_z$ wherein x is an integer from 1 to 3, suitably 1 or 2, Y is an anion, suitably a halogen anion, and z is an integer from 0 to 3, suitably 1 or 2. Suitably the metal species (M) are transition metal atoms or ions. Suitably the metal species (M) are first row transition metal atoms or ions. Suitably the metal species (M) are selected from atoms or ions of Co, Cu, Zn and Ni. Suitably the metal species (M) are Co ions, Cu ions or Ni ions, suitably $Co^{2+}$, $Cu^{2+}$ ions or $Ni^{2+}$ ions. Suitably the metal species (M) are Cu ions, suitably $Cu^{2+}$ ions. In some embodiments the metal species (M) are Ni ions, suitably $Ni^{2+}$ ions, or Co ions, suitably $Co^{2+}$. Suitably all metal species (M) in the hybrid porous material are the same.

In the first sorbent material, the metal species (M) are linked together in a first and second dimension by first linker groups ($L^1$). One of $L^1$ and $L^2$ is an organic linker group and the other of $L^1$ and $L^2$ is an inorganic linker group. In other words either the first linker groups ($L^1$) are organic linkers and the second linker groups ($L^2$) are inorganic linkers, or the first linker groups ($L^1$) are inorganic linkers and the second linker groups ($L^2$) are organic linkers. Therefore the first linker groups ($L^1$) may be organic linkers or inorganic linkers. Alternatively, in materials comprising halide anions (z=1 to 3), $L^1$ and $L^2$ can be both organic linkers.

Suitably the first linker groups ($L^1$) are organic linkers. Preferably the first linker groups ($L^1$) comprise at least two donor atoms. Donor atoms are atoms present within the linker group which have a lone election pair which can be donated, for example in the formation of a metal-ligand complex. This lone electron pair is suitably donated to the metal species on formation of the hybrid porous material. The donor atoms may be charged or neutral species, for example a donor atom may in fact be present as an ion such as an oxygen atom of a carboxylate species.

Suitably the donor atoms in the organic linkers are selected from halogens, oxygen and nitrogen. A suitable organic linker may comprise N-oxide groups which provide an oxygen donor atom. The two or more donor atoms may each be the same or different.

Suitably the donor atoms are selected from oxygen and nitrogen. Preferably all the donor atoms are nitrogen.

Suitably the first linker groups ($L^1$) are nitrogen ligands comprising at least two donor atoms which are nitrogen atoms. Suitably the at least two nitrogen atoms each comprise a lone pair of electrons suitable for binding to a metal species. Therefore the nitrogen ligands are suitably two-connected nitrogen ligands. By "two-connected" we mean the nitrogen ligand is capable of binding to two different metal species (M) in the hybrid porous material. In preferred embodiments the lone pairs of electrons on the two nitrogen atoms are in orbitals orientated away from each other at an angle capable of forming a lattice, for example an angle greater than 90°, for example an angle of approximately 120° or an angle of approximately 180°.

Suitably the two nitrogen atoms in the two-connected nitrogen ligands are separated by from 2.5 to 20 Å, for example separated by from 2.5 to 10 Å or from 10 to 20 Å.

Suitably the first linker groups ($L^1$) are two-connected nitrogen ligands. Preferred two-connected nitrogen ligands comprise at least one nitrogen-containing heterocycle. In some embodiments the two-connected nitrogen ligand may be a nitrogen-containing heterocycle comprising two nitrogen atoms each having a lone pair of electrons, for example pyrazine.

In some embodiments the two-connected nitrogen ligand comprises two nitrogen-containing heterocycles. The two nitrogen-containing heterocycles may be linked together by a bond. One such preferred two-connected nitrogen ligand is 4,4'-bipyridine.

Alternatively, the two nitrogen-containing heterocycles may be linked together by a spacer group, for example acetylene. One such preferred two-connected nitrogen ligand is 4,4'-bipyridylacetylene. Suitably the first linker groups ($L^1$) are two-connected nitrogen ligands having the formula (L2N):

(L2N)

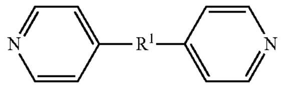

wherein $R^1$ is an optionally substituted linker group.

$R^1$ may be a heteroatom, a group of connected heteroatoms or a group comprising heteroatoms. For example $R^1$ may be a —N═N— group.

$R^1$ may be a hydrocarbyl group. The hydrocarbyl group may comprise a cyclic group. The hydrocarbyl group may comprise an aromatic cyclic group. The hydrocarbyl group may comprise a heterocyclic group.

As used herein, the term "hydrocarbyl" is used in its ordinary sense, which is well-known to those skilled in the art. Specifically, it refers to a group having predominantly hydrocarbon character. Examples of hydrocarbyl groups include:

(i) hydrocarbon groups, that is, aliphatic (which may be saturated or unsaturated, linear or branched, e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

(ii) substituted hydrocarbon groups, that is, substituents containing non-hydrocarbon groups which, in the context of this invention, do not alter the predominantly hydrocarbon nature of the substituent (e.g., halo (especially chloro and fluoro), hydroxy, alkoxy, keto, acyl, cyano, mercapto, alkylmercapto, amino, alkylamino, nitro, nitroso, and sulphoxy);

(iii) hetero substituents, that is, substituents which, while having a predominantly hydrocarbon character, in the context of this invention, contain other than carbon in a ring or chain otherwise composed of carbon atoms. Heteroatoms include sulphur, oxygen, nitrogen, and encompass substituents as pyridyl, furyl, thienyl and imidazolyl.

Suitable two-connected nitrogen ligands may be selected from pyrazine, 4,4'-bipyridine and from 4,4'-bipyridylacetylene and compounds (LA) to (LFF):

(LA)

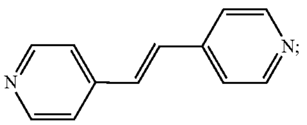

(LB)

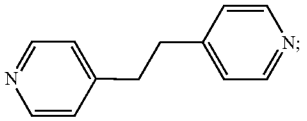

(LC)

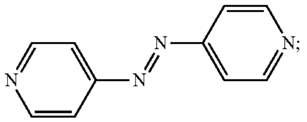

(LD)

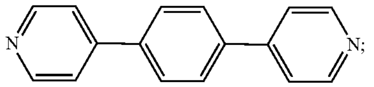

-continued (LE)

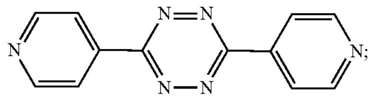

(LF)

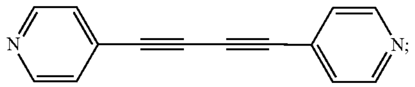

(LG)

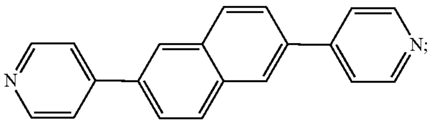

(LH)

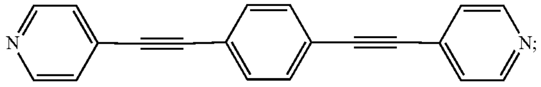

(LI)

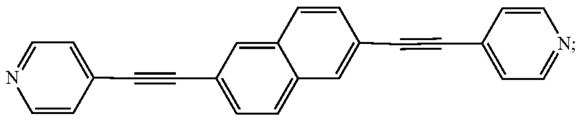

(LJ)

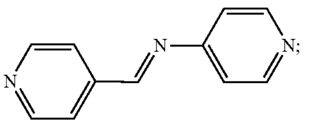

(LK)

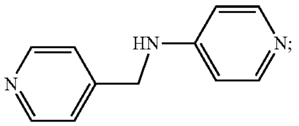

(LL)

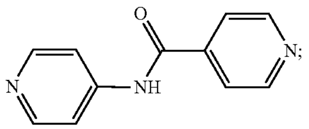

(LM)

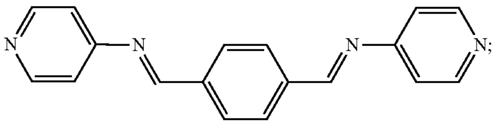

(LN)

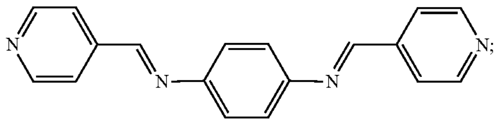

(LO)

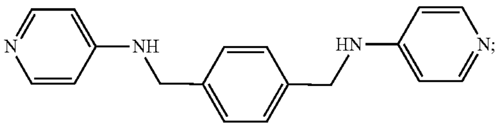

(LP)

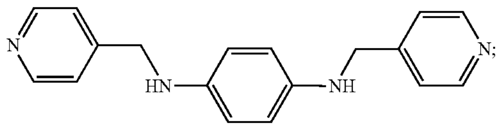

-continued
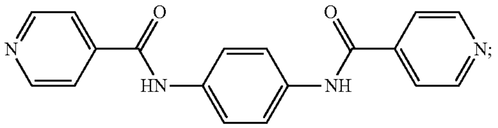
(LQ)
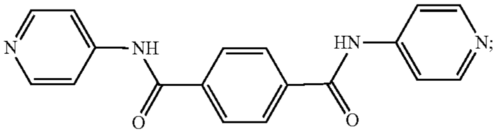
(LR)
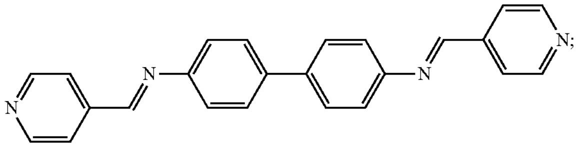
(LS)
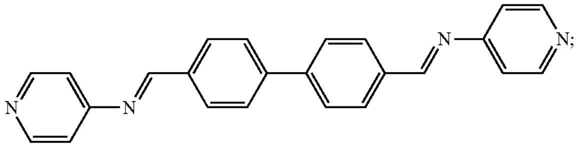
(LT)
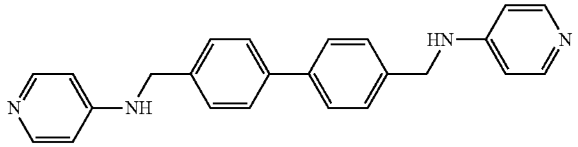
(LU)
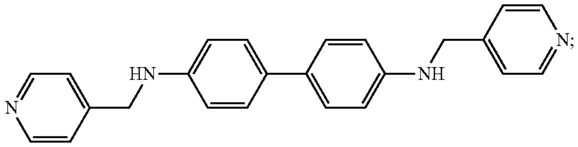
(LV)
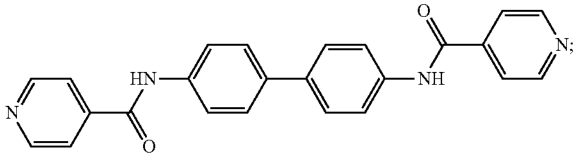
(LW)
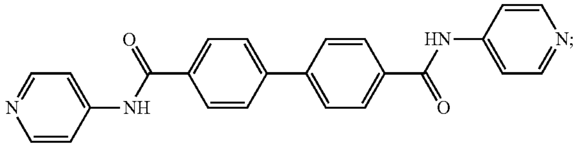
(LX)
-continued
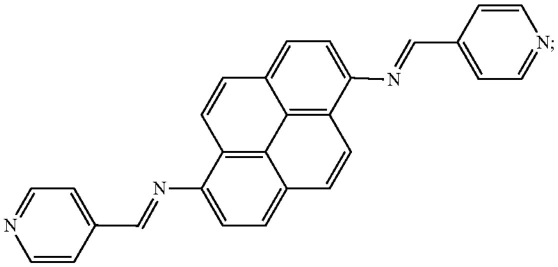
(LY)
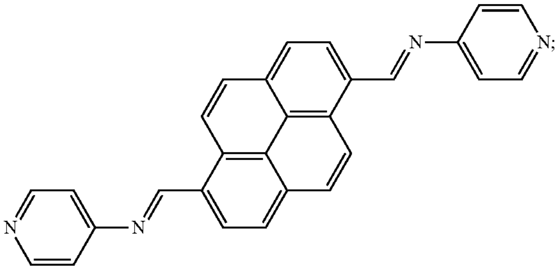
(LZ)
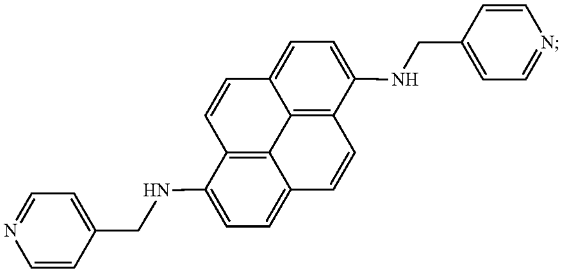
(LAA)
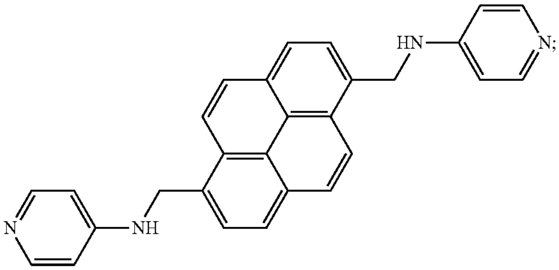
(LBB)
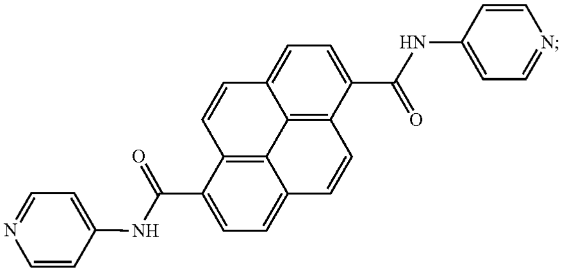
(LCC)

-continued (LDD)

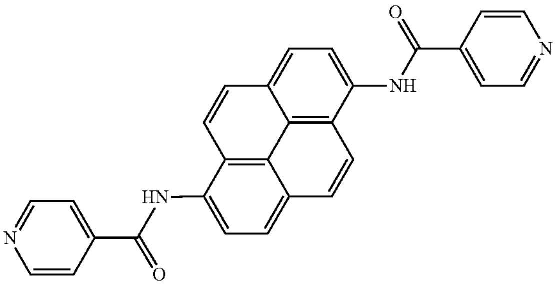

(LEE)

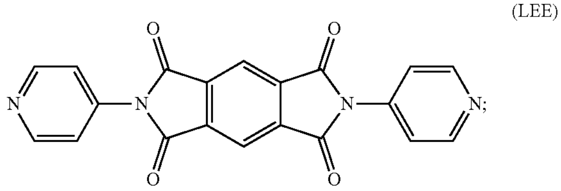

(LFF)

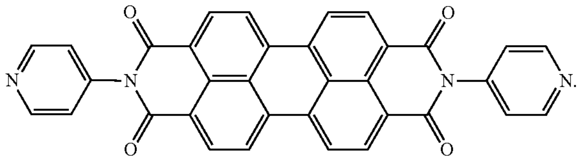

Suitably the first linker groups ($L^1$) are two-connected nitrogen ligands selected from pyrazine, 4,4'-bipyridine and 4,4'-bipyridylacetylene. Suitably the first linker groups ($L^1$) are selected from 4,4'-bipyridylacetylene and 4,4'-bipyridine. Suitably the first linker groups ($L^1$) is 4,4'-bipyridylacetylene.

Suitably all first linker groups ($L^1$) in the hybrid porous material are the same.

The metal species (M) are linked together in a first and second dimension by the first linker groups ($L^1$). Suitably the first and second dimensions are substantially perpendicular to one another. Suitably the first linker groups ($L^1$) link together the metal species (M) to form a two-dimensional layer having a square planar repeating unit of formula (I):

(I)

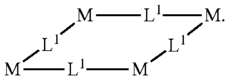

The metal species (M) are linked together in a third dimension by second linker groups ($L^2$) to form a three-dimensional lattice. Suitably the second linker groups ($L^2$) are capable of forming an interaction between two different metal species. Typically the metal species form a two-dimensional layer with first linker groups ($L^1$), for example a two-dimensional layer of square planar repeating units, for example of formula (I).

Suitably the second linker groups ($L^2$) form an interaction with two different metal species in two different layers. Suitably the second linker groups ($L^2$) are capable of forming interactions with two different atoms or ions of metal species (M) in order to form a three-dimensional lattice. For example the second linker groups ($L^2$) are capable of forming interactions with two different atoms or ions of metal species (M) which are orientated at an angle to each other of greater than 90°, for example an angle of approximately 120° or an angle of approximately 180°.

Suitably the second linker groups ($L^2$) are inorganic linkers. Suitably each second linker group ($L^2$) includes at least two donor atoms. Suitable donor atoms include halogens, oxygen, nitrogen and sulphur. Preferred donor atoms of the second linker groups ($L^2$) are halogens, especially chlorine or fluorine, preferably fluorine. Suitably the second linker groups ($L^2$) comprise at least one halogen or chalcogen (Group VIA) atom. Preferably the second linker groups ($L^2$) comprise at least one fluorine or oxygen atom.

Suitably the second linker groups ($L^2$) are inorganic compounds comprising at least one fluorine atom. Suitably the second linker groups ($L^2$) are charged, suitably anions. Suitably the second linker groups ($L^2$) are inorganic anions comprising at least one fluorine atom. Preferably the second linker groups ($L^2$) comprise at least two halogen atoms. Preferably the second linker groups ($L^2$) comprise at least two fluorine atoms.

Suitably the second linker groups ($L^2$) are compounds of formula $AX_n^{y-}$, wherein X is selected from F or Cl, n is an integer from 2 to 6, y is an integer from 0 to 2 and A is selected from Si, Ti, Sn, Zr or Ge. Suitably n is an integer from 4 to 6. Preferably n is 6. Preferably y is 2. Suitably X is F. Suitably the second linker groups ($L^2$) are selected from $SiF_6^{2-}$, $TiF_6^{2-}$, $SnF_6^{2-}$, $ZrF_6^{2-}$ and $GeF_6^{2-}$. Suitably the second linker groups ($L^2$) are selected from $SiF_6^{2-}$, $TiF_6^{2-}$ and $SnF_6^{2-}$. Suitably the second linker groups ($L^2$) are ions of $TiF_6^{2-}$.

In some embodiments, the second linker groups ($L^2$) are organic linkers wherein each second linker group ($L^2$) includes at least two donor atoms. Suitable donor atoms include oxygen, nitrogen and sulphur. Preferred donor atoms of the second linker groups ($L^2$) are oxygen atoms, especially from carboxylate groups, or nitrogen atoms, especially from azolate groups. Suitably the second linker groups ($L^2$) comprise at least chalcogen (Group VIA) atom or pnictogen (Group VA). Preferably the second linker groups ($L^2$) comprise at least oxygen atom or nitrogen atom.

In such embodiments, the second linker groups ($L^2$) may be carboxylic acids, for example di-carboxylic acid compounds or ions. Such second linker groups ($L^2$) may be selected from chiral or racemic tartaric acid, malic acid, succinic acid, fumaric acid, 2,3-dibromosuccinic acid, aspartic acid, 1,4-benzenedicarboxylic acid and 1,3-benzenedicarboxylic acid. The second linker group ($L^2$) may be L-tartaric acid (L-tart).

Suitably all second linker groups ($L^2$) in the hybrid porous material are the same.

Suitably the second linker groups ($L^2$) link the metal species (M) of different two dimensional layers having a repeating unit of formula (I) to form the three-dimensional lattice. Suitably the three-dimensional lattice of metal species (M) and linker groups has a cubic lattice structure, suitably a primitive cubic lattice structure. Suitably the three-dimensional lattice of metal species (M) and linker groups ($L^1$ and $L^2$) comprises the repeating unit (unit cell) of formula (II):

(II)

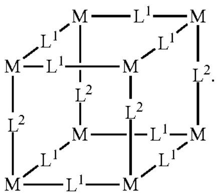

Suitably the three-dimensional lattice of metal species (M) and linker groups consists essentially of repeating units of formula (II).

Suitably the metal species (M) are selected from $Co^{2+}$ and/or from $Cu^{2+}$, $Ni^{2+}$ and $Zn^{2+}$ ions, the first linker groups ($L^1$) are selected from 4,4'-bipyridylacetylene, 4,4'-bipyridine and pyrazine and the second liker groups ($L^2$) are selected from $SiF_6^{2-}$, $TiF_6^{2-}$, $SnF_6^{2-}$, $ZrF_6^{2-}$ and $GeF_6^{2-}$.

Preferably the metal species (M) are selected from $Cu^{2+}$, $Ni^{2+}$ and $Zn^{2+}$ ions, the first linker groups ($L^1$) are selected from 4,4'-bipyridylacetylene, 4,4'-bipyridine and pyrazine and the second liker groups ($L^2$) are selected from $SiF_6^{2-}$, $TiF_6^{2-}$ and $SnF_6^{2-}$ ions.

Suitably the metal species (M) are $Cu^{2+}$ ions, the first linker groups ($L^1$) are selected from 4,4'-bipyridylacetylene and 4,4'-bipyridine and the second liker groups ($L^2$) are $TiF_6^{2-}$ ions.

The first sorbent material may be prepared by any suitable method, for example by solid state synthesis, crystallisation from a suitable solvent, direct mixing, slurrying or mechanochemistry, each with or without heating. For example, the hybrid porous material may be prepared by any of the above methods by reacting an approximately equimolar amount of the metal species (M), for example a salt of the metal species (M), the first linker group ($L^1$), for example a two-connected nitrogen ligand, and the second linker group ($L^2$), for example a salt of an $AX_n^{y-}$ anion, optionally together in a suitable solvent, for example a mixture of water and methanol, optionally with heating.

In some embodiments, the three-dimensional lattice of metal species (M) and linker groups ($L^1$ and $L^2$) may be interpenetrated. By interpenetrated we mean that two or more three-dimensional lattices of metal species (M) and linker groups are interlocked so that they cannot be separated without breaking chemical bonds, for example as shown in structure (III) wherein the first three-dimensional lattice comprises M, $L^1$ and $L^2$ and the second three-dimensional lattice comprises M', $L^{1'}$ and $L^{2'}$:

(III)

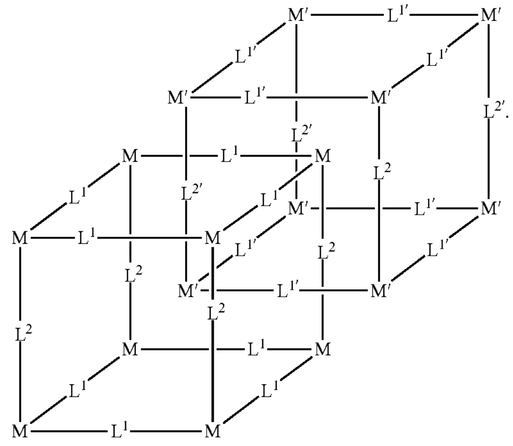

Whether a hybrid porous material forming reaction, such as those described above, forms an interpenetrated hybrid porous material or a non-interpenetrated hybrid porous material may depend on the particular reaction type and/or the solvent used (if any) and/or the temperature of the reaction and/or the concentration of the reaction mixture, as described in "Temperature and Concentration Control over Interpenetration in a Metal-Organic Material" (Zaworotko, M. J. et al, J. Am. Chem. Soc., 2009, 131, 17040-17041) and "Template-directed synthesis of metal-organic materials" (Zaworotko, M. J. and Zhang, Z., Chem. Soc. Rev., 2014, 43, 5444).

The three-dimensional lattice of metal species (M) and linker groups, which provides the hybrid porous material used in the method of this first aspect, comprises pores. The pores are formed in the sections of the three-dimensional lattice defined by M, $L^1$ and $L^2$. Therefore in the method, acetylene may pass through openings of the pores in the hybrid porous material defined by M, $L^1$ and $L^2$ and become bound to the three-dimensional lattice within said pores. It is believed that the size of said pores may contribute to the selectivity and capacity exhibited by the hybrid porous materials of the present invention.

Suitably the hybrid porous material comprises pores with an effective pore size of from 3.5 to 12 Å.

Effective pore size may be additionally or alternatively defined as the effective pore diameter. Effective pore size/diameter is a measure of the dimensions of the pore at the narrowest point of the pore. These values take into account the van der Waals radii of the atoms lining the pore wall (i.e. they are not atom to atom distances).

In alternative embodiments the first linker groups ($L^1$) are inorganic linkers and are as defined above in relation to the second linker groups ($L^2$), and the second linker groups ($L^2$) are organic linkers and are as defined above in relation to the first linker groups ($L^1$). In other words, in the hybrid porous material used in the method of the first aspect, the above definitions of the first linker groups ($L^1$) and the second linker groups ($L^2$) may be interchanged.

The first sorbent material is selected according to the above description in order to have selectivity for acetylene over ethylene, and suitably over ethane and carbon dioxide. Suitably the metal species (M) are $Cu^{2+}$ ions, the first linker groups ($L^1$) are 4,4'-bipyridylacetylene, the second liker groups ($L^2$) are $TiF_6^{2-}$ ions and the three-dimensional lattice of metal species (M) and linker groups is interpenetrated. This particular hybrid porous material may be known as TIFSIX-2-Cu-i.

In some embodiments, the first sorbent material has the chemical formula: $M_x(L^1)_2(L^2)Y_z$ wherein the metal species (M) is selected from atoms or ions of Co, Cu, Zn and Ni, wherein x is an integer from 1 to 3, $L^1$ is a two-connected nitrogen ligand as defined above, $L^2$ is a dicarboxylic acid, Y is an anion and z is an integer from 0 to 3. Suitably $L^2$ is a $C_{2-10}$ dicarboxylic acid. Suitably $L^2$ is selected from chiral or racemic tartaric acid, malic acid, succinic acid, fumaric acid, 2,3-dibromosuccinic acid, aspartic acid, 1,4-benzenedicarboxylic acid and 1,3-benzenedicarboxylic acid.

Suitably the metal species (M) are $Co^{2+}$ or $Ni^{2+}$ ions, suitably $Ni^{2+}$ ions, the first linker groups ($L^1$) are 4,4'-bipyridine and the second linker groups ($L^2$) are tartaric acid ions, suitably L-tartaric acid ions. In addition, halide anions are bridging the metal species. This particular hybrid porous material may be known as $[Ni_2(bpy)_2(L\text{-}tart)F_2]$.

In such embodiments, the first sorbent material may be $[Ni_2(bpy)_2(L\text{-}tart)F_2]$.

The Second Sorbent Material

The second sorbent material is suitably a porous material which has a higher adsorption selectivity for ethane than for ethylene and/or acetylene, and suitably carbon dioxide.

Suitably the second sorbent material is an ultramicroporous material which has a higher adsorption selectivity for ethane than for ethylene and acetylene, and suitably also for carbon dioxide.

Suitably the second sorbent material is an ultramicroporous material comprising pores which are hydrophobic or weakly hydrophilic. Suitably the pores of the second sorbent material are more hydrophobic than the pores of the first sorbent material, and any third or further sorbent material present. Such a hydrophobic pore nature suitably provides adsorption selectivity for ethane over ethylene, acetylene and suitably carbon dioxide. The inventors have found that such hydrophobic pores may provide only weak van der Waals or hydrogen bond interactions which may therefore preferentially bind to relatively non-polar molecules such as ethane.

Suitably the pores of the second sorbent have an average size of less than 0.7 nm, for example of less than 0.6 nm or less than 0.5 nm.

Suitably the second sorbent material has the chemical formula: $M_2(L^1)_2(L^2)$. Suitably the second sorbent material is formed by metal ions, carboxylate ligands and azolate ligands, appropriately selected in order to provide selectivity for ethane over ethylene, and suitably over acetylene and carbon dioxide. Suitable azolate ligands include imidazolate and triazolate ligands.

Suitably the second sorbent material is a Zn-based framework material, suitably of formula $Zn_2(A)_2(B)$.

A is suitably selected from amino-substituted heterocyclic ligands comprising at least two donor atoms which are nitrogen atoms. Suitably the at least two nitrogen atoms each comprise a lone pair of electrons suitable for binding to a metal species. A is suitably selected from amino-substituted heterocyclic ligands comprising at least three donor atoms which are nitrogen atoms. Suitably A is an ionic compound. Suitably A is a triazolate ion.

Suitably A is an ion derived from 3-amino-1,2,4-triazole (Hatz, formula (III)), an ion derived from 3,5-diamino-1,2,4-triazole (Hdatz, formula (IV)) or an ion derived from 1,2,4-triazole (V).

(III)

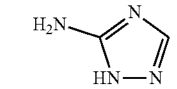

(IV)

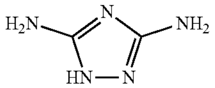

(V)

B is suitably selected from dicarboxylate ligands. Suitably B is a dicarboxylate ligand comprising at least one phenyl group. Suitably B is an ion derived from isophthalic acid ($H_2$ipa, formula (VI)) or 4,4'-oxobisbenzoic acid ($H_2$oba, formula (VII)).

(VI)

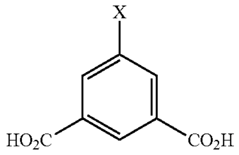

(VII)

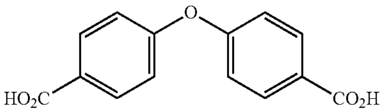

Compound (VI) may be optionally substituted at the 5-position. For example, the X group may be selected from $C_1$-$C_4$ alkyl, $C_1$-$C_4$ alkoxy, $C_1$-$C_4$ alkylamino, $C_1$-$C_4$ alkylthio, hydroxy, amino, nitro, thiol, bromo, chloro, fluoro, $CF_3$, $CHF_2$ or $CH_2F$ groups. Suitably X is selected from H, $NH_2$, $NO_2$, F, Cl, Br, methyl or ethyl.

Suitably A is an ion derived from 3-amino-1,2,4-triazole and B is an ion derived from isophthalic acid. Therefore the second sorbent material is suitably $Zn_2(atz)_2(ipa)$. This material may be referred to as Zn-atz-ipa. This material is as described in Kai-Ji Chen et al in "New Zn-Aminotriazolate-Dicarboxylate Frameworks: Synthesis, Structures and Adsorption Properties", *Cryst. Growth Des.,* 2013, 13, 2118-2123.

In some embodiments, the second sorbent material is suitably an ultramicroporous material of formula $M(L^1)_2(L^2)$ as defined above for the first sorbent material, which may additionally comprise anions such as halogen ions, where appropriate. Therefore the first sorbent may have the formula $M_x(L^1)_2(L^2)Y_z$, wherein M is a transition metal cation, wherein x is an integer from 1 to 3, suitably 1 or 2, Y is an anion, suitably a halogen anion, and z is an integer from 0 to 3, suitably 1 or 2. Suitably the second sorbent material is an ultramicroporous material of formula $M_2(L^1)_2(L^2)Y_2$, wherein Y is a halogen anion, suitably $F^-$, suitably wherein M is $Co^{2+}$ or $Ni^{2+}$ and $L^1$ is as described in relation to the first sorbent material. Suitably $L^2$ is a di-carboxylic acid as defined above in relation to linker B of $Zn_2(A)_2(B)$, or a di-carboxylic acid equivalent linker with an azolate group, for example tetrazolate, triazolate, pyrazolate, imidazolate, such as Tzba which is derived from 4-(1H-tetrazol-5-yl)benzoic acid (structure VIII below).

(VIII)

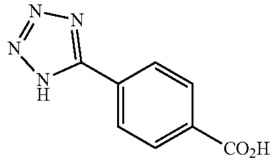

In such embodiments, the second sorbent material may be $[Co_2(bpy)_2(Tzba)F_2]$.

Suitably the first sorbent material is TIFSIX-2-Cu-i and the second sorbent material is Zn-atz-ipa. Therefore the first aspect of the present invention may provide a method of obtaining a target gas, such as ethylene or methane, from a gaseous composition comprising the target gas, acetylene and ethane, the method comprising the step of contacting the gaseous composition with a sorbent media to remove at least some of the acetylene and at least some of the ethane from the gaseous composition; wherein the sorbent media comprises TIFSIX-2-Cu-i and Zn-atz-ipa; wherein the TIFSIX-2-Cu-i selectively adsorbs the acetylene over the target gas and the ethane; and wherein the Zn-atz-ipa selectively adsorbs the ethane over the target gas and the acetylene.

Additionally or alternatively, the first sorbent material may be $[Ni_2(bpy)_2(L\text{-tart})F_2]$ and/or the second sorbent material may be $[Co_2(bpy)_2(Tzba)F_2]$, to carry out the method described herein. Therefore in some embodiments, the first sorbent material may be selected from TIFSIX-2-Cu-i and $[Ni_2(bpy)_2(L\text{-tart})F_2]$, and the second sorbent material may be selected from Zn-atz-ipa and $[Co_2(bpy)_2(Tzba)F_2]$. In the following description, $[Ni_2(bpy)_2(L\text{-tart})F_2]$ may replace TIFSIX-2-Cu-i and/or $[Co_2(bpy)_2(Tzba)F_2]$ may replace Zn-atz-ipa.

It is believed that in TIFSIX-2-Cu-i, $C_2H_2$, $C_2H_4$ and $C_2H_6$ molecules localize so that every molecule can interact with two $TiF_6^{2-}$ anions through C—HF interactions. However, $C_2H_2$ has shorter contacts with distances of 2.46 and 2.50 Å compared to $C_2H_4$ (2.45 and 2.52 Å) and $C_2H_6$ (2.62 and 2.90 Å). Moreover, the more acidic $C_2H_2$ molecule (pKa=26, vs $C_2H_4$, pKa=45, and $C_2H_6$, pKa=62) may form stronger hydrogen bonding interactions. For TIFSIX-2-Cu-i, $CO_2$ molecules interact with two F atoms from one $TiF_6^{2-}$ anion, with short interaction distances between the C atom of $CO_2$ and F atoms of $TiF_6^{2-}$ anion (2.65 and 3.48 Å). It is therefore thought that the interaction strengths in TIFSIX-2-Cu-i is $C_2H_2>CO_2>C_2H_4>C_2H_6$.

The inventors have also unexpectedly found that Zn-atz-ipa and $[Co_2(bpy)_2(Tzba)F_2]$ selectively adsorbs ethane. Without being bound by theory, it is thought that the all six hydrogen atoms present in one molecule of ethane interact with the pore surface of Zn-atz-ipa, giving rise to a tight-fitting binding site. Smaller molecules such as carbon dioxide and ethylene do not have as many contact points and so the binding site does not fit as closely. As such these small molecules are not as tightly bound. The strength of interactions in Zn-atz-ipa thus follows the sequence $C_2H_6>C_2H_4>C_2H_2>CO_2$. Likewise, $[Co_2(bpy)_2(Tzba)F_2]$ selectively adsorbs $C_2H_6$ over $C_2H_4$ and $CO_2$.

In such embodiments the sorbent media may comprise TIFSIX-2-Cu-i and Zn-atz-ipa in a weight ratio of from 1:1 to 1:20 TIFSIX-2-Cu-i to Zn-atz-ipa, suitably of from 1:5 to 1:15, for example a weight ratio of approximately 1:10 TIFSIX-2-Cu-i to Zn-atz-ipa.

In alternative embodiments, the second sorbent material may have the formula $M(C_2N_3H_2)_2$ wherein M is selected from Mg, Mn, Fe, Co, Cu or Zn. Suitably the second sorbent material is formed by metal ions and triazole, suitably 1H-1,2,3-triazole, appropriately selected in order to provide selectivity for ethane over ethylene, and suitably over acetylene and carbon dioxide. These materials may be referred to as MET framework materials. These materials are as described in Felipe Gándara et al in "Porous, Conductive Metal-Triazolates and Their Structural Elucidation by the Charge-Flipping Method", *Chem. Eur. J.,* 2012, 18, 10595-10601.

Suitably the second sorbent material has the formula $Mn(C_2N_3H_2)_2$, wherein the ligand is 1H-1,2,3-triazole. This material may be referred to as MET-2.

Suitably the second sorbent material has the formula $Cu(C_2N_3H_2)_2$, wherein the ligand is 1H-1,2,3-triazole. This material may be referred to as MET-5.

Suitably the second sorbent material has the formula $Zn(C_2N_3H_2)_2$, wherein the ligand is 1H-1,2,3-triazole. This material may be referred to as MET-6.

Suitably the first sorbent material is TIFSIX-2-Cu-i and the second sorbent material is a MET framework material, suitably selected from MET-2, MET-5 and MET-6. Therefore the first aspect of the present invention may provide a method of obtaining a target gas, such as ethylene or methane, from a gaseous composition comprising the target gas, acetylene and ethane, the method comprising the step of contacting the gaseous composition with a sorbent media to remove at least some of the acetylene and at least some of the ethane from the gaseous composition; wherein the sorbent media comprises TIFSIX-2-Cu-i and a MET framework material; wherein the TIFSIX-2-Cu-i selectively adsorbs the acetylene over the target gas and the ethane; and wherein the MET framework material selectively adsorbs the ethane over the target gas and the acetylene.

In such embodiments the sorbent media may comprise TIFSIX-2-Cu-i and a MET framework material in a weight ratio of from 1:1 to 1:20 TIFSIX-2-Cu-i to the MET framework material, suitably of from 1:5 to 1:15, for example a weight ratio of approximately 1:10 TIFSIX-2-Cu-i to the MET framework material.

The Third Sorbent Material

In some embodiments, the gaseous composition comprises a third gas, suitably carbon dioxide. In such embodiments, the gaseous mixture suitably comprises, consists essentially of or consists of the target gas, acetylene, ethane and carbon dioxide. In such embodiments, the sorbent media comprises the first and second sorbent materials as described above and a third sorbent material, wherein the third sorbent material has a higher adsorption selectivity for the third gas than for the target gas. Suitably the third sorbent material has a higher adsorption selectivity for the third gas than for target gas, the first gas and the second gas. The third gas is suitably carbon dioxide and therefore the third sorbent material suitably has a higher adsorption selectivity for carbon dioxide than for the target gas, suitably ethylene or methane. The third sorbent material suitably has a higher adsorption selectivity for carbon dioxide than for the target gas and acetylene. The third sorbent material suitably has a higher adsorption selectivity for carbon dioxide than for the target gas, acetylene and ethane. The third sorbent is different to the first and second sorbents.

The third sorbent material is suitably an ultramicroporous material as defined above wherein one of $L^1$ and $L^2$ is an organic linker group and the other of $L^1$ and $L^2$ is an inorganic linker group, which has a higher adsorption selectivity for carbon dioxide than for the target gas, acetylene and ethane. The third sorbent material may be appropriately selected from the ultramicroporous materials described in relation to the first sorbent material.

Suitably the third sorbent material has the chemical formula: $M(L^1)_2(L^2)$. Suitably the metal species (M) are transition metal atoms or ions. Suitably the metal species (M) are $Ni^{2+}$ ions. Suitably the first linker groups ($L^1$) are pyrazine. Suitably the second linker groups ($L^2$) are $SiF_6^{2-}$ ions.

In the third sorbent material, the metal species (M) are $Ni^{2+}$ ions, the first linker groups ($L^1$) are pyrazine, the second liker groups ($L^2$) are $SiF_6^{2-}$ ions and the three-dimensional lattice of metal species (M) and linker groups is not interpenetrated. This particular hybrid porous material may be known as SIFSIX-3-Ni.

In some embodiments, the first sorbent material is TIFSIX-2-Cu-i, the second sorbent material is Zn-atz-ipa and the third sorbent material is SIFSIX-3-Ni. Therefore the first aspect of the present invention may provide a method of obtaining a target gas, for example ethylene or methane, from a gaseous composition comprising the target gas, acetylene, ethane and carbon dioxide, the method comprising the step of contacting the gaseous composition with a sorbent media to remove at least some of the acetylene, at least some of the ethane and at least some of the carbon dioxide from the gaseous composition; wherein the sorbent media comprises TIFSIX-2-Cu-i, Zn-atz-ipa and SIFSIX-3-Ni; wherein the TIFSIX-2-Cu-i selectively adsorbs the acetylene over the target gas, ethane and carbon dioxide; wherein the Zn-atz-ipa selectively adsorbs the ethane over the taget gas, acetylene and carbon dioxide; and wherein the SIFSIX-3-Ni selectively adsorbs the carbon dioxide over the target gas, acetylene and ethane. Suitably the method removes substantially all of the acetylene, ethane and carbon dioxide from the gaseous composition to provide the target gas in high purity, for example a purity of at least 95 wt %, suitably at least 99 wt %, suitably at least 99.9 wt %, suitably at least 99.99 wt %.

It is thought that in SIFSIX-3-Ni, $CO_2$ binding is driven by interactions with four electronegative F atoms from four independent $SiF_6^{2-}$ anions. $C_2H_2$ is trapped through multiple C—HF interactions with HF distances of 3.3-4.5 Å between $C_2H_2$ and eight $SiF_6^{2-}$ anions. In contrast, $C_2H_4$ and $C_2H_6$ exhibit simultaneous interactions with two and six $SiF_6^{2-}$ anions, respectively. Though there are fewer contacts with anions, shorter interaction distances of 2.51 and 2.62 Å for $C_2H_4$ suggest that the adsorption energy of $C_2H_4$ will be favourable vs. $C_2H_6$ (2.59-2.76 Å). Thus SIFSIX-3-Ni preferentially adsorbs $CO_2>C_2H_2>C_2H_4>C_2H_6$.

In such embodiments the sorbent media may comprise a weight ratio of TIFSIX-2-Cu-i to SIFSIX-3-Ni of from 2:1 to 1:2, suitably from 1.5:1 to 1:1.5, suitably approximately 1:1.25. The sorbent media may comprise TIFSIX-2-Cu-i, Zn-atz-ipa and SIFSIX-3-Ni in a weight ratio of approximately 1/1.25/10, suitable for use with an industrial gas mixture.

In alternative embodiments, the first sorbent material is TIFSIX-2-Cu-i, the second sorbent material is a MET framework material and the third sorbent material is SIFSIX-3-Ni. Therefore the first aspect of the present invention may provide a method of obtaining a target gas, for example ethylene or methane, from a gaseous composition comprising the target gas, acetylene, ethane and carbon dioxide, the method comprising the step of contacting the gaseous composition with a sorbent media to remove at least some of the acetylene and at least some of the ethane from the gaseous composition; wherein the sorbent media comprises TIFSIX-2-Cu-i, a MET framework material and SIFSIX-3-Ni; wherein the TIFSIX-2-Cu-i selectively adsorbs the acetylene over the target gas, ethane and carbon dioxide; wherein the MET framework material selectively adsorbs the ethane over the target gas, acetylene and carbon dioxide; and wherein the SIFSIX-3-Ni selectively adsorbs the carbon dioxide over the target gas, acetylene and ethane.

In such embodiments the sorbent media may comprise a weight ratio of TIFSIX-2-Cu-i to SIFSIX-3-Ni of from 2:1 to 1:2, suitably from 1.5:1 to 1:1.5, suitably approximately 1:1.25. The sorbent media may comprise TIFSIX-2-Cu-i, a MET framework material and SIFSIX-3-Ni a weight ratio of approximately 1/1.25/10.

The inventors have found that these combinations of first, second and third sorbent materials can provide the target gas, such as ethylene or methane, in high purity from a gaseous composition comprising the target gas, acetylene, ethane and carbon dioxide.

The contacting of the gaseous composition with the sorbent media may be carried out at any suitable temperature below 120° C., suitably at a temperature of from −20° C. to 60° C., suitably of from 0° C. to 50° C., suitably from 0° C. to 40° C., suitably from 10° C. to 40° C. The contacting of the gaseous composition with the sorbent media may be carried out at ambient temperature. Such a temperature may also be referred to as room temperature. The temperature of this step may be chosen according to the selectivity profile of the first, second and third (if present) sorbent materials for the first, second or third gas (if present) respectively at different temperatures of said gases.

The method being able to function effectively at ambient temperature may provide cost and/or energy savings and may therefore provide a significant advantage over methods of the prior art.

The contacting of the gaseous composition with the sorbent media may be carried out at a pressure of from 0.1 to 5 bar, suitably from 0.4 to 2 bar, for example from 0.5 bar to 1.5 bar or approximately 1 bar. Suitably the contacting of the gaseous composition with the sorbent media is carried out at a pressure of 1 bar. The pressure of this step may be chosen according to the selectivity profile of the first, second and third (if present) sorbent materials for the first, second or third gas (if present) respectively at different pressures of said gases.

In embodiments wherein the gaseous composition comprises acetylene, ethylene, ethane and carbon dioxide, the partial pressures of these gases are suitably acetylene 1%, ethylene 33%, ethane 33% and carbon dioxide 33%, of the total pressure of the gaseous composition. Therefore the partial pressures of the different gases are suitably acetylene 0.01 bar, ethylene 0.33 bar, ethane 0.33 bar and carbon dioxide 0.33 bar, wherein the gaseous mixture has a pressure of approximately 1 bar.

Suitably the method of this first aspect is carried out under ambient pressure. The method being able to function effectively at ambient pressure may lead to significant cost and/or energy savings and may avoid the use of complex equipment, which may be advantageous over some methods of the prior art.

The method of the first aspect suitably provides the target gas, such as ethylene or methane in a higher purity than some methods of the prior art. Suitably the present invention provides the target gas with a purity of at least 95 wt %, suitably at least 99 wt %, suitably at least 99.9 wt %, suitably at least 99.99 wt %.

The method of the first aspect suitably provides ethylene in a high purity suitable for polymer manufacture, suitably in a higher purity than some methods of the prior art. Suitably the present invention provides ethylene with a purity of at least 95 wt %, suitably at least 99 wt %, suitably at least 99.9 wt %, suitably at least 99.99 wt %.

The method of the first aspect involves obtaining a target gas from a gaseous composition comprising the target gas, a first gas and a second gas, the method comprising the step of contacting the gaseous composition with a sorbent media. Therefore the method of the first aspect may be considered to involve the steps of:

a) providing a gaseous composition comprising a target gas, a first gas and a second gas;
b) contacting the gaseous composition with a sorbent media comprising a first sorbent material and a second sorbent material, to remove at least some of the first gas and at least some of the second gas from the gaseous composition; wherein the first sorbent material has a higher adsorption selectivity for the first gas than for the target gas and the second sorbent material has a higher adsorption selectivity for the second gas than for the target gas; and
c) collecting the target gas from the sorbent media.

Suitably the steps of the method are carried out in the order step a) followed by step b) followed by step c).

Suitably the target gas is ethylene or methane.

In some embodiments, the target gas is ethylene. Suitably the method of the first aspect involves obtaining ethylene from a gaseous composition comprising ethylene, a first gas and a second gas, the method comprising the step of contacting the gaseous composition with a sorbent media.

Therefore the method of the first aspect may be considered to involve the steps of:

a) providing a gaseous composition comprising ethylene, a first gas and a second gas;
b) contacting the gaseous composition with a sorbent media comprising a first sorbent material and a second sorbent material, to remove at least some of the first gas and at least some of the second gas from the gaseous composition; wherein the first sorbent material has a higher adsorption selectivity for the first gas than for ethylene and the second sorbent material has a higher adsorption selectivity for the second gas than for ethylene; and
c) collecting ethylene from the sorbent media.

The method may be a continuous process whereby the gaseous mixture is directed into contact with the sorbent media in a suitable vessel and ethylene is collected from the sorbent media once the first and second gases have been adsorbed by the sorbent media.

The method may involve, after step c), a step d) of removing the first gas and the second gas from the sorbent media. This may be considered to be a regeneration of the sorbent media. Suitably the sorbent media can be regenerated after each use, to be used again in the method of the first aspect, for example in a second or further sequence of steps a) to c). Regenerating the sorbent media suitably involves removing the first and second gases, and any third or further gases if present, from the sorbent media onto or into which these gases have been adsorbed during step b). This may be achieved by heating for sorbent media and/or flowing a diluent gas through the sorbent media. For example, the sorbent material may be regenerated at a temperature of 60° C. under He flow. Suitably the regeneration takes place for up to 2 hours, for example up to 1 hour. Suitably the regeneration takes less than 10 minutes. Suitably the regeneration takes place until the acetylene hydrocarbon and $CO_2$ signal in a mass spectrum of effluent gas has disappeared.

Therefore the method may involve, after step d), repeating steps a) to c). Suitably the sorbent material may be used more than once in a repeat of steps a) to c). Suitably the sorbent material may be used at least twice or three times with no or minimal loss in adsorption performance. Suitably the sorbent material may be used at least 10 times with no or minimal loss in adsorption performance. Suitably the sorbent material may be used 50 times with no or minimal loss in adsorption performance. Suitably the sorbent material may be used more than 50 times whilst still providing sufficient adsorption performance to purify the target gas to the levels of purity discussed above.

According to a third aspect of the present invention, there is provided a method of removing ethane from a gaseous composition, the method comprising the step of contacting the gaseous composition with a sorbent material to remove at least some of the ethane, wherein the sorbent material comprises an ultramicroporous material of formula $Zn_2(A)_2(B)$; wherein A is an amino-substituted heterocyclic ligand and B is a dicarboxylate ligand. Therefore the sorbent material suitably is $Zn_2(atz)_2(ipa)$.

The method, gaseous composition and sorbent material of this third aspect may have any of the suitable features and advantages described in relation to the first aspect.

The method, gaseous composition and sorbent material of this third aspect may have any of the suitable features and advantages described in relation to the first aspect.

Suitably the pores of the sorbent material are hydrophobic or weakly hydrophilic. The sorbent material may have any of the suitable features or advantages of the second sorbent material described in relation to the first and second aspects of the present invention.

The gaseous composition suitably comprises ethylene and ethane, suitably ethylene, ethane and acetylene, suitably ethylene, ethane, acetylene and carbon dioxide. The gaseous composition may have any of the suitable features or advantages of the gaseous composition described in relation to the first and second aspects of the present invention.

In some embodiments, the gaseous composition comprises methane and ethane, suitably methane, ethane and acetylene, suitably methane, ethane, acetylene and carbon dioxide.

The method of removing ethane from a gaseous composition of this third aspect may have any of the suitable features or advantages of the method of obtaining ethylene from a gaseous composition comprising ethylene, a first gas and a second gas, of the first aspect of the present invention.

According to a fourth aspect of the present invention, there is provided a use of an ultramicroporous material of formula $Zn_2(A)_2(B)$; wherein A is an amino-substituted heterocyclic ligand and B is a dicarboxylate ligand, to separate ethane from a gas mixture comprising ethane.

The use of this fourth aspect may have any of the features and advantages described in relation to the third aspect, and therefore the first and second aspects.

According to a fifth aspect of the present invention, there is provided a method of removing ethane from a gaseous composition, the method comprising the step of contacting the gaseous composition with a sorbent material to remove at least some of the ethane, wherein the sorbent material comprises an ultramicroporous material of formula $M_x(L^1)_2(L^2)Y_z$ wherein M is $Co^{2+}$ or $Ni^{2+}$, wherein x is an integer from 1 to 3, $L^1$ is an organic linker group, $L^2$ is a di-carboxylic acid linker or a di-carboxylic acid equivalent linker having an azolate group, Y is an inorganic anion and z is an integer from 0 to 3.

The method, gaseous composition and sorbent material of this fifth aspect may have any of the suitable features and advantages described in relation to the first aspect.

Suitably the ultramicroporous material is $[Co_2(bpy)_2(Tzba)F_2]$.

Suitably the pores of the sorbent material are hydrophobic or weakly hydrophilic. The sorbent material may have any of the suitable features or advantages of the second sorbent material described in relation to the first and second aspects of the present invention.

The gaseous composition suitably comprises ethylene and ethane, suitably ethylene, ethane and acetylene, suitably ethylene, ethane, acetylene and carbon dioxide. The gaseous composition may have any of the suitable features or advantages of the gaseous composition described in relation to the first and second aspects of the present invention.

In some embodiments, the gaseous composition comprises methane and ethane, suitably methane, ethane and acetylene, suitably methane, ethane, acetylene and carbon dioxide.

The method of removing ethane from a gaseous composition of this fifth aspect may have any of the suitable features or advantages of the method of obtaining ethylene from a gaseous composition comprising ethylene, a first gas and a second gas, of the first aspect of the present invention.

According to a sixth aspect of the present invention, there is provided a use of an ultramicroporous material of formula $M_x(L^1)_2(L^2)Y_z$ wherein M is $Co^{2+}$ or $Ni^{2+}$, wherein x is an integer from 1 to 3, $L^1$ is an organic linker group, $L^2$ is a di-carboxylic acid linker or a di-carboxylic acid equivalent linker having an azolate group, Y is an inorganic anion and z is an integer from 0 to 3, to separate ethane from a gas mixture comprising ethane.

The use of this sixth aspect may have any of the features and advantages described in relation to the fifth aspect, and therefore the first and second aspects.

According to a seventh aspect of the present invention, there is provided a method of removing acetylene from a gaseous composition, the method comprising the step of contacting the gaseous composition with a sorbent material to remove at least some of the acetylene, wherein the sorbent material comprises an ultramicroporous material of formula: $M_x(L^1)_2(L^2)Y_z$ wherein the metal species (M) is selected from atoms or ions of Co, Cu, Zn and Ni, wherein x is an integer from 1 to 3, $L^1$ is a two-connected nitrogen ligand as defined above, $L^2$ is a dicarboxylic acid, Y is an anion and z is an integer from 0 to 3. Suitably $L^2$ is a $C_{2-10}$ dicarboxylic acid. Suitably $L^2$ is selected from chiral or racemic tartaric acid, malic acid, succinic acid, fumaric acid, 2,3-dibromosuccinic acid, aspartic acid, 1,4-benzenedicarboxylic acid and 1,3-benzenedicarboxylic acid.

The method, gaseous composition and sorbent material of this seventh aspect may have any of the suitable features and advantages described in relation to the first aspect.

Suitably the sorbent material comprises $[Ni_2(bpy)_2(L\text{-}tart)F_2]$. Suitably the sorbent material is $[Ni_2(bpy)_2(L\text{-}tart)F_2]$.

The gaseous composition suitably comprises ethylene and acetylene, suitably ethylene, ethane and acetylene, suitably ethylene, ethane, acetylene and carbon dioxide. The gaseous composition may have any of the suitable features or advantages of the gaseous composition described in relation to the first and second aspects of the present invention.

In some embodiments, the gaseous composition comprises methane, ethane and acetylene, suitably methane, ethane, acetylene and carbon dioxide.

The method of removing acetylene from a gaseous composition of this seventh aspect may have any of the suitable features or advantages of the method of obtaining ethylene from a gaseous composition comprising ethylene, a first gas and a second gas, wherein the first gas is acetylene, of the first aspect of the present invention.

According to an eighth aspect of the present invention, there is provided a use of an ultramicroporous material of formula $M_x(L^1)_2(L^2)Y_z$ to separate ethane from a gas mixture comprising ethane, wherein the metal species (M) is selected from atoms or ions of Co, Cu, Zn and Ni, wherein x is an integer from 1 to 3, $L^1$ is a two-connected nitrogen ligand as defined above, $L^2$ a dicarboxylic acid, Y is an anion and z is an integer from 0 to 3. Suitably $L^2$ is a $C_{2-10}$ dicarboxylic acid. Suitably $L^2$ is selected from chiral or racemic tartaric acid, malic acid, succinic acid, fumaric acid, 2,3-dibromosuccinic acid, aspartic acid, 1,4-benzenedicarboxylic acid and 1,3-benzenedicarboxylic acid.

The use of this eighth aspect may have any of the features and advantages described in relation to the seventh aspect, and therefore the first and second aspects.

Suitably the sorbent material comprises $[Ni_2(bpy)_2(L\text{-}tart)F_2]$. Suitably the sorbent material is $[Ni_2(bpy)_2(L\text{-}tart)F_2]$.

According to a ninth aspect of the present invention, there is provided a sorbent media comprising a first sorbent material and a second sorbent material; wherein the first sorbent material has a higher adsorption selectivity for a first gas than for a target gas; wherein the second sorbent material has a higher adsorption selectivity for a second gas than for the target gas; and wherein the first sorbent material and the second sorbent material are different ultramicroporous materials.

The gaseous composition and sorbent media may have any of the suitable features and advantages described in relation to the first and second aspects.

According to a tenth aspect of the present invention, there is provided an apparatus for obtaining a target gas from a gaseous composition comprising the target gas, a first gas and a second gas, the apparatus comprising a sorbent media according to the ninth aspect.

The sorbent media is suitably arranged on the support in a configuration to ensure maximum adsorption. Suitably the apparatus comprises means for directing the gaseous composition through or across the sorbent material.

In some embodiments the device may be electrically powered. Suitably the apparatus is powered by renewable resources.

In some embodiments the target gas provided by the method, use or apparatus described herein may undergo further treatment. In alternative embodiments the target gas provided by the method, use or apparatus described herein may be used directly in a subsequent process.

For example, wherein the target gas is ethylene, the ethylene may be used directly in the production of poly(ethylene) and other related polymers.

In the methods of the present invention, if water vapour is present in the gaseous mixture then a desiccant material may be used to remove said water vapour. The gaseous mixture may be contacted with a desiccant material before or after contacting the sorbent media.

According to an eleventh aspect of the present invention, there is provided an ultramicroporous material of formula $[Co_2(bpy)_2(Tzba)F_2]$.

According to a twelfth aspect of the present invention, there is provided a sorbent media comprising $[Co_2(bpy)_2(Tzba)F_2]$.

The sorbent media may have any of the suitable features and advantages described herein, particularly with reference to the sorbent media of the ninth aspect.

The invention will now be further described by reference to the accompanying figures and examples.

EXAMPLES

In the following examples, the following materials were used:

Materials

Ammonium hexafluorotitanate($(NH_4)_2TiF_6$, 99.99%, Sigma-Aldrich), ammonium hexafluorosilicate ($(NH_4)_2SiF_6$, 99.999%, Sigma-Aldrich), copper (II) tetrafluoroborate hydrate ($Cu(BF_4)_2 \cdot xH_2O$, Sigma-Aldrich), zinc nitrate hexahydrate ($Zn(NO_3)_2 \cdot 6H_2O$, 98%, Sigma-Aldrich), nickel(II) nitrate hexahydrate ($Ni(NO_3)_2 \cdot 6H_2O$, Sigma-Aldrich), isophthalic acid ($C_8H_6O_4$, 99%, TCI), 3-amino-1,2,4-triazole ($C_2H_4N_4$, 98%, TCI), pyrazine ($C_4H_4N_2$, 99%, Sigma-Aldrich) and solvents (DMF and methanol, HPLC grade of 99.9%) from Sigma-Aldrich were purchased and directly used.

He (99.999%), $CO_2$ (99.999%), $N_2$ (99.9995%), $C_2H_2$ (98.5%), $C_2H_4$ (99.92%) and $C_2H_6$ (99%) were purchased from BOC gases Ireland.

Methods

Synthesis of TIFSIX-2-Cu-i

This material was synthesized according to the method described in K.-J. Chen et al., *Chem* 1, 753-765 (2016).

An aqueous solution (60 mL) obtained from dissolving 2.4 g of $Cu(BF_4)_2 \cdot xH_2O$ and 2.0 g of $(NH_4)_2TiF_6$ was added into a methanol solution (60 mL) dissolving 2.07 g of 4,4'-bipyridylacetylene. This mixture was transferred to a 200 mL borosilicate bottle, and then heated at 80° C. for 24 hours. After heating, the mixture was filtrated and the light-green powder was harvested. The powder was exchanged with fresh methanol twice a day for three days. Yield: 65% based on ligand.

Synthesis of Zn-atz-ipa

This material was synthesized based on the method described in K.-J. Chen et al., *Cryst. Growth Des.* 13, 2118-2123 (2013).

Mixing of $Zn(NO_3)_2 \cdot 6H_2O$ (20 mmol, 5.96 g), $H_2$ipa (10 mmol, 1.66 g), Hatz (20 mmol, 1.68 g) in a solvent mixture of DMF (60 mL), MeOH (60 mL), and $H_2O$ (30 mL) afforded a suspension solution, followed by three minutes of sonication. Then this mixture was capped in a 250 mL borosilicate bottle and heated at 130° C. for 72 hours, which was followed by slow cooling process to room temperature with 10° C./hour. After cooling, the mother liquor was decanted and the colorless crystalline product can be harvested by filtration. The white sample was rinsed three times with fresh DMF of 20 mL and dried in air. Yield: 55% based on metal salt.

Synthesis of Zn-datz-ipa

This material was synthesized based on the method described in K.-J. Chen et al., *Cryst. Growth Des.* 13, 2118-2123 (2013).

Synthesis of MET-2, MET-5 and MET-6

These materials were synthesized based on the method describe in Felipe Gándara et al in "Porous, Conductive Metal-Triazolates and Their Structural Elucidation by the Charge-Flipping Method", Chem. Eur. J., 2012, 18, 10595-10601.

Synthesis of SIFSIX-3-Ni

This material was synthesized using the method described in A. Kumar et al., *Angew. Chem. Int. Ed.* 54, 14372-14377 (2015).

By keeping stirring a slurry mixture of 437 mg (1.5 mmol) of $Ni(NO_3)_2 \cdot 6H_2O$, 269 mg (1.5 mmol) of $(NH_4)_2SiF_6$ and 240 mg (3 mmol) of pyrazine in 3 mL of water for 3 days, a microcrystalline powder in purple was harvested. The suspension mixture was filtered and purple powder was then soaked in methanol for one day, followed by two more washing by 10 ml methanol. After this, SIFSIX-3-Ni was formed through a heating operation by degassing this purple sample under high vacuum at 100° C. for 24 hours. Yield: 85% based on ligand.

Powder X-Ray Diffraction Experiments

Powder X-ray diffraction experiments were carried out using a PANalytical Empyrean diffractometer equipped with a PIXcel3D detector operating in the scanning line detector mode with an active length of 4 utilizing 255 channels. Cu $K_{\alpha 12}$ radiation was used for the diffraction experiments.

Single-Gas Sorption Experiments

Micromeritics Tristar II 3030 and 3 Flex 3500 instruments were used for collecting the sorption isotherms at 77 K for $N_2$ and 273 or 298 K for $C_2H_2$, $C_2H_4$, $C_2H_6$ and $CO_2$. A 4 L Dewar filled with liquid $N_2$ was adopted for temperature control at 77 K. Precise control of 273 and 298 K were realized by a Julabo ME (v.2) with a recirculating control system containing a mixture of ethylene glycol and water. Before adsorption analysis, MeOH-exchanged samples were fully degassed under high vacuum (<0.5 mmHg) at different conditions: TIFSIX-2-Cu-i (40° C. for 16 hours), SIFSIX-3-Ni (100° C. for 24 hours) and Zn-atz-ipa (120° C. for 18 hours). The apparent BET surface areas of Zn-atz-ipa and TIFSIX-2-Cu-i were determined from 77 K $N_2$ adsorption isotherms. 273 K $CO_2$ adsorption isotherms were used to calculate BET surface area for SIFSIX-3-Ni as $N_2$ is unable to diffuse readily into narrow pores of SIFSIX-3-Ni at 77 K and $CO_2$ can fill the pore channel even at 273 K. At every interval of two independent isotherms for any material, the sorbent was regenerated by 5 hours degassing under high vacuum at 30° C. before commencement of the next sorption experiment.

Dynamic Breakthrough Experiments

In a three-gas breakthrough experiment, ca. 0.85 g of pre-activated single sample, tandem-packed or mixed samples was placed in quartz tubing (8 mm diameter) to form a fixed bed.

The adsorbent bed was purged under a 25 $cm^3$/min flow of He gas at 90° C. for 1 hour before the breakthrough experiment. Upon cooling to 25° C., a 2.1 $cm^3$/min gas mixture containing 33.3% $C_2H_2$, 33.3% $C_2H_4$ and 33.3% $C_2H_6$ gas was introduced. The outlet composition was continuously monitored by mass spectrometry (MS) until complete breakthrough was achieved. When outlet composition of four gases reaches equilibrium, gas mixture flow was then shut off and a gas flow (10 $cm^3$/min) of He gas was introduced to regenerate the adsorption bed at <60° C. In order to examine the sorbent material performance at practical conditions, a 1.4 $cm^3$/min gas mixture containing 1% $C_2H_2$, 49.5% $C_2H_4$ and 49.5% $C_2H_6$ gas was also used during breakthrough studies for four gas mixture.

In a four-gas breakthrough experiment, ca. 1.47 g of pre-activated tandem-packed or mixed samples were placed in quartz tubing (8 mm diameter) to form a fixed bed. Two different gas mixtures having the following compositions: 25% $C_2H_2$/25% $C_2H_4$/25% $C_2H_6$/25% $CO_2$ and 1% $C_2H_2$/33% $C_2H_4$/33% $C_2H_6$/33% $CO_2$ were introduced at 2.8 $cm^3$/min.

In recycling tests, the sample was regenerated after each experiment under He flow of 10 $cm^3$/min at 60° C. for ca. one hour or until the disappearance of $C_2$ hydrocarbon and $CO_2$ signals in MS.

Pure Gas Adsorption Measurements

To evaluate the aforementioned sorbents for $C_2H_4$ separation processes, the pure gas adsorption properties of each sorbent were investigated.

Figure 2:
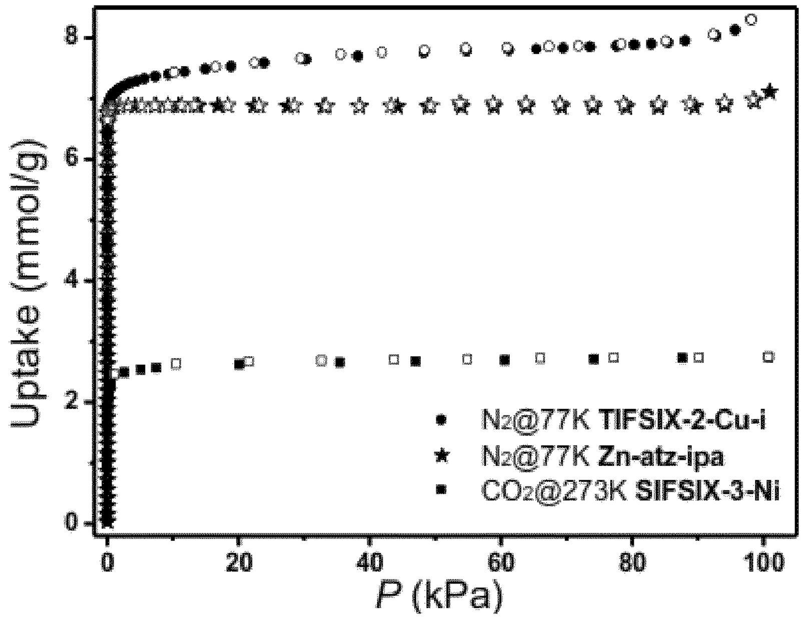
FIG. 2: Graph showing single-gas sorption data for TIFSIX-2-Cu-i, SIFSIX-3-Ni and Zn-atz-ipa.
Figure 3:
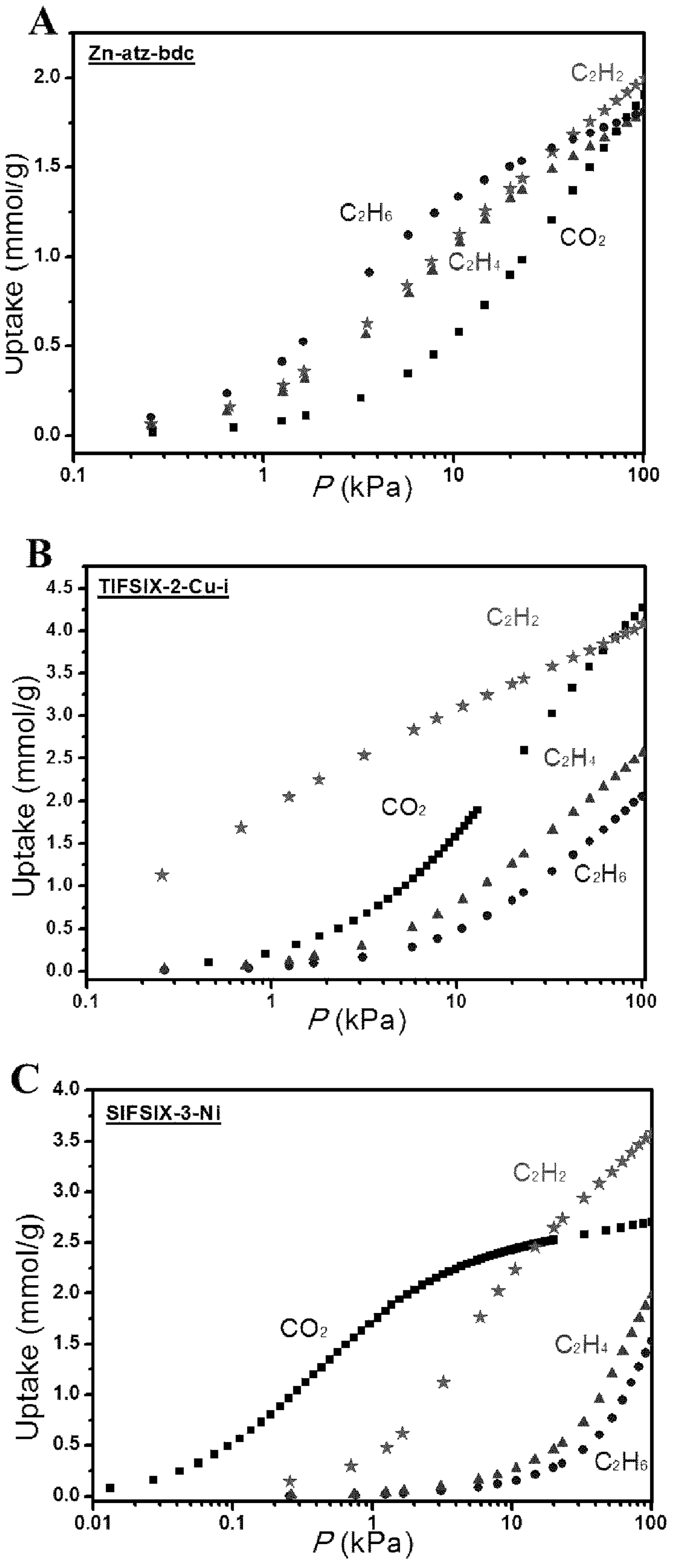
FIG. 3: Graphs showing single-gas ($C_2H_2$, $C_2H_4$, $C_2H_6$ and $CO_2$) sorption data for Zn-atz-ipa (FIG. 3, panel A). TIFSIX-2-Cu-i (FIG. 3, panel B) and SIFSIX-3-Ni (FIG. 3, panel C).
Figure 4:
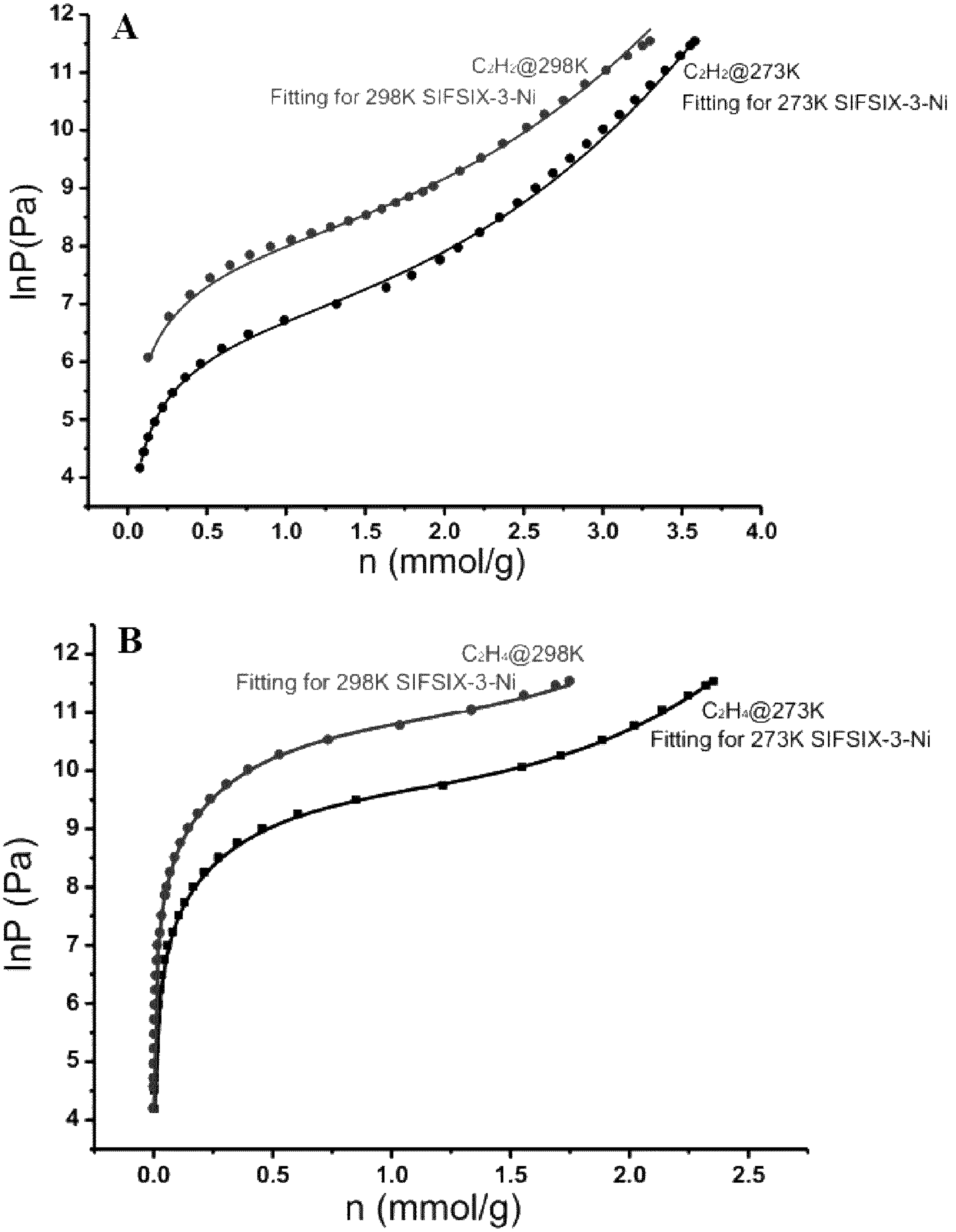
FIG. 4: Graphs showing virial fitting of $C_2H_2$ (FIG. 4, panel A) and $C_2H_4$ (FIG. 4, panel B) sorption data for SIFSIX-3-Ni.
Figure 5:
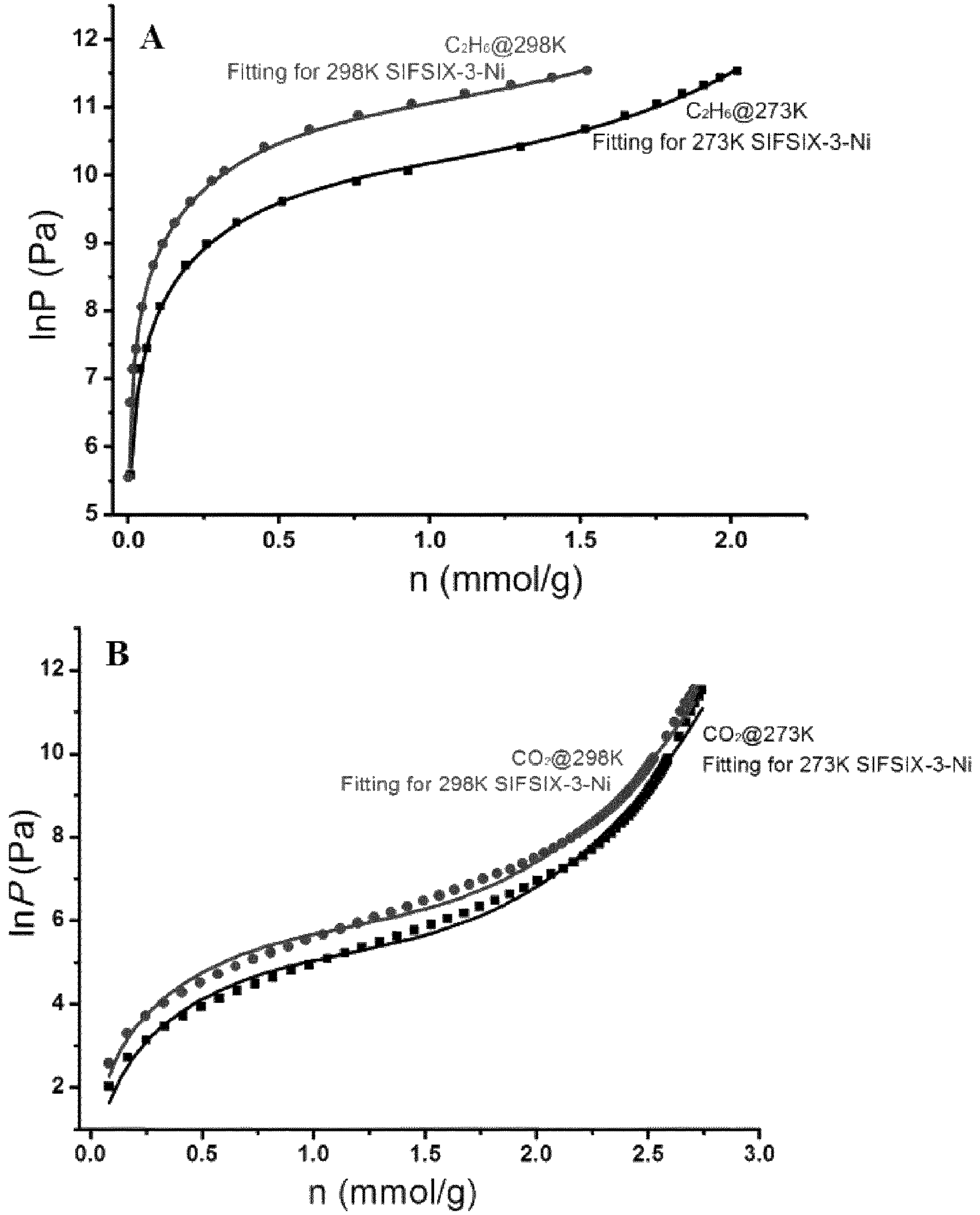
FIG. 5: Graphs showing virial fitting of $C_2H_6$ (FIG. 5, panel A) and $CO_2$ (FIG. 5, panel B) sorption data for SIFSIX-3-Ni.
Figure 6:
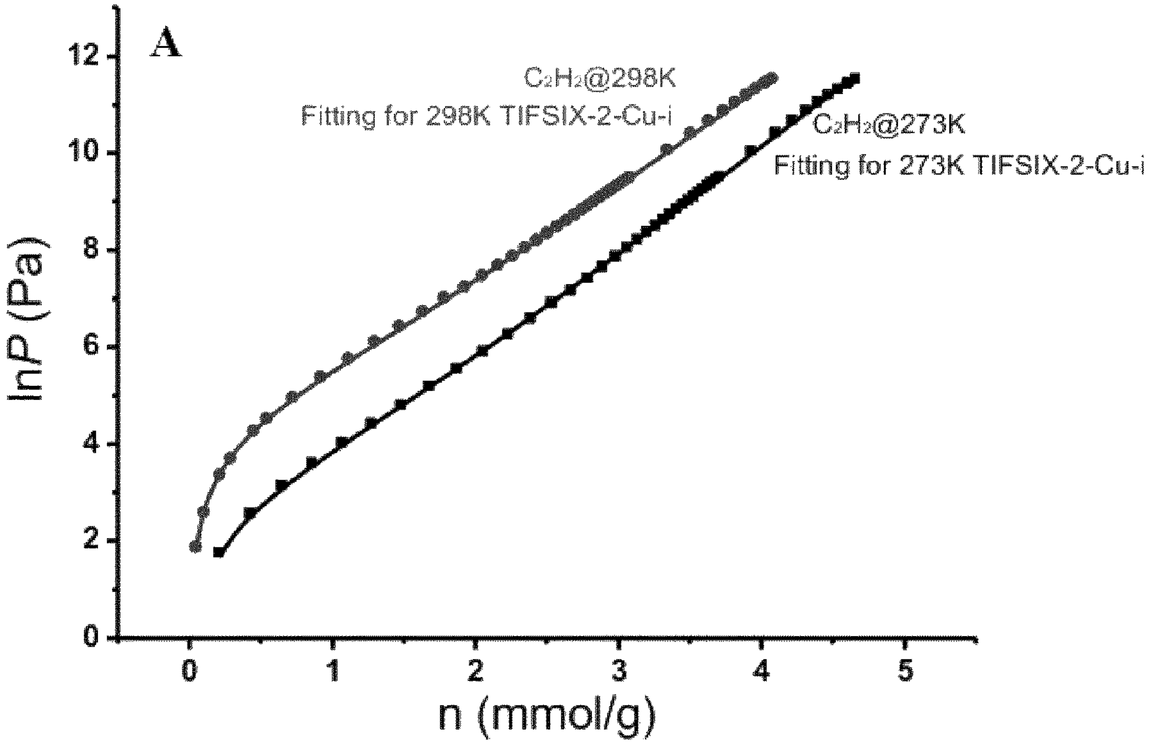
FIG. 6: Graphs showing virial fitting of $C_2H_2$ (FIG. 6, panel A) and $C_2H_4$ (FIG. 6, panel B) sorption data for TIFSIX-2-Cu-i.
Figure 6:
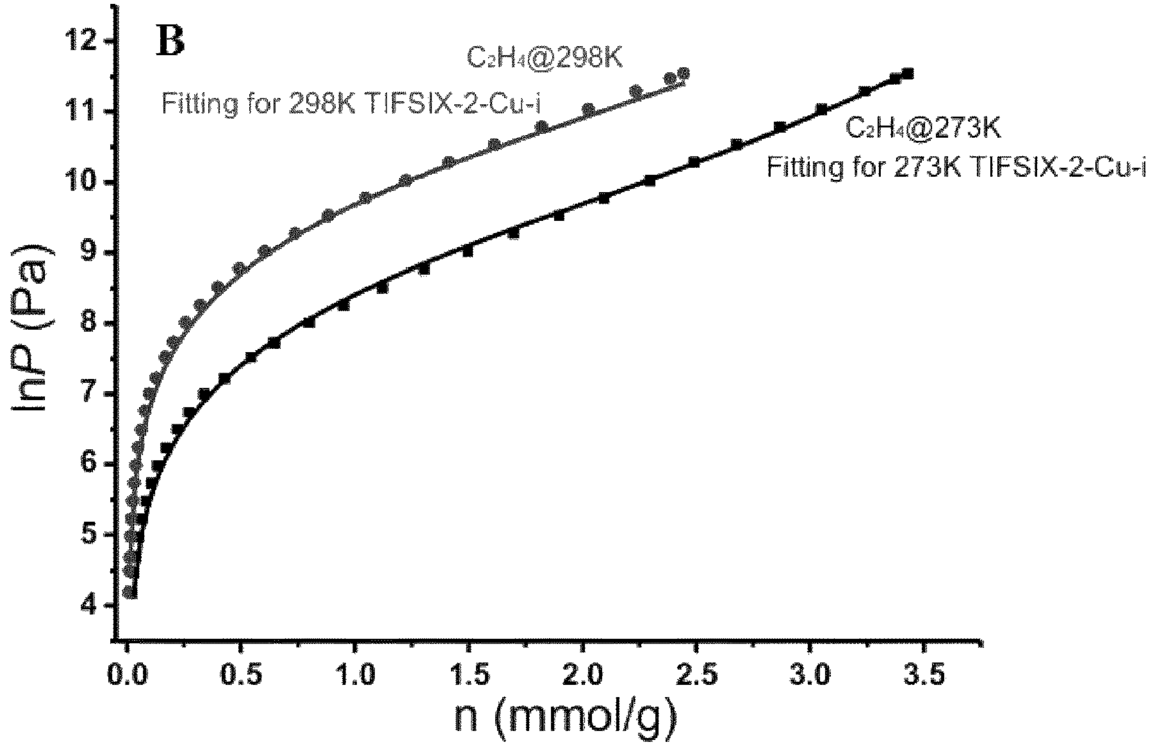
Figure 7:
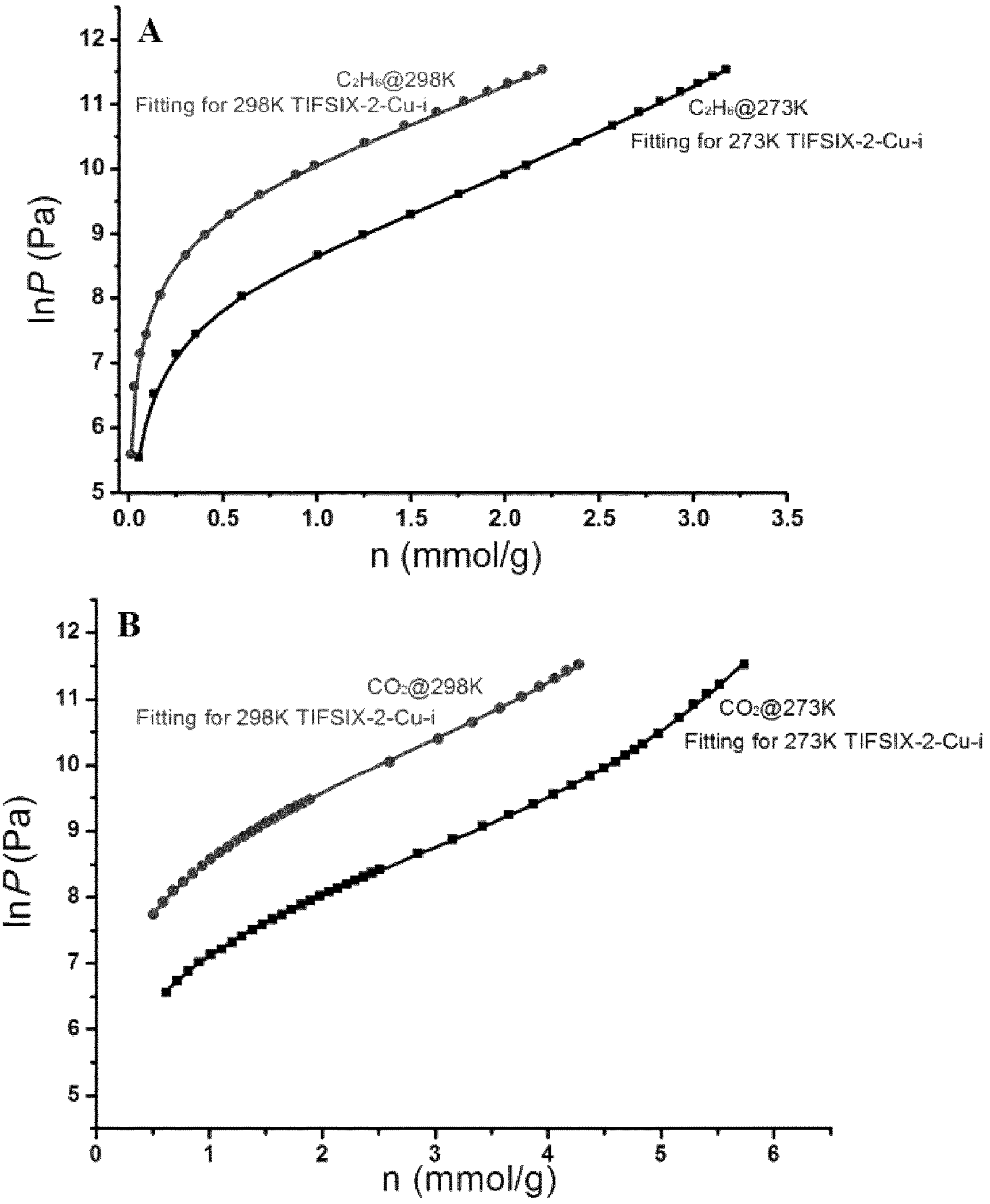
FIG. 7: Graphs showing virial fitting of $C_2H_6$ (FIG. 7, panel A) and $CO_2$ (FIG. 7, panel B) sorption data for TIFSIX-2-Cu-i.
Figure 8:
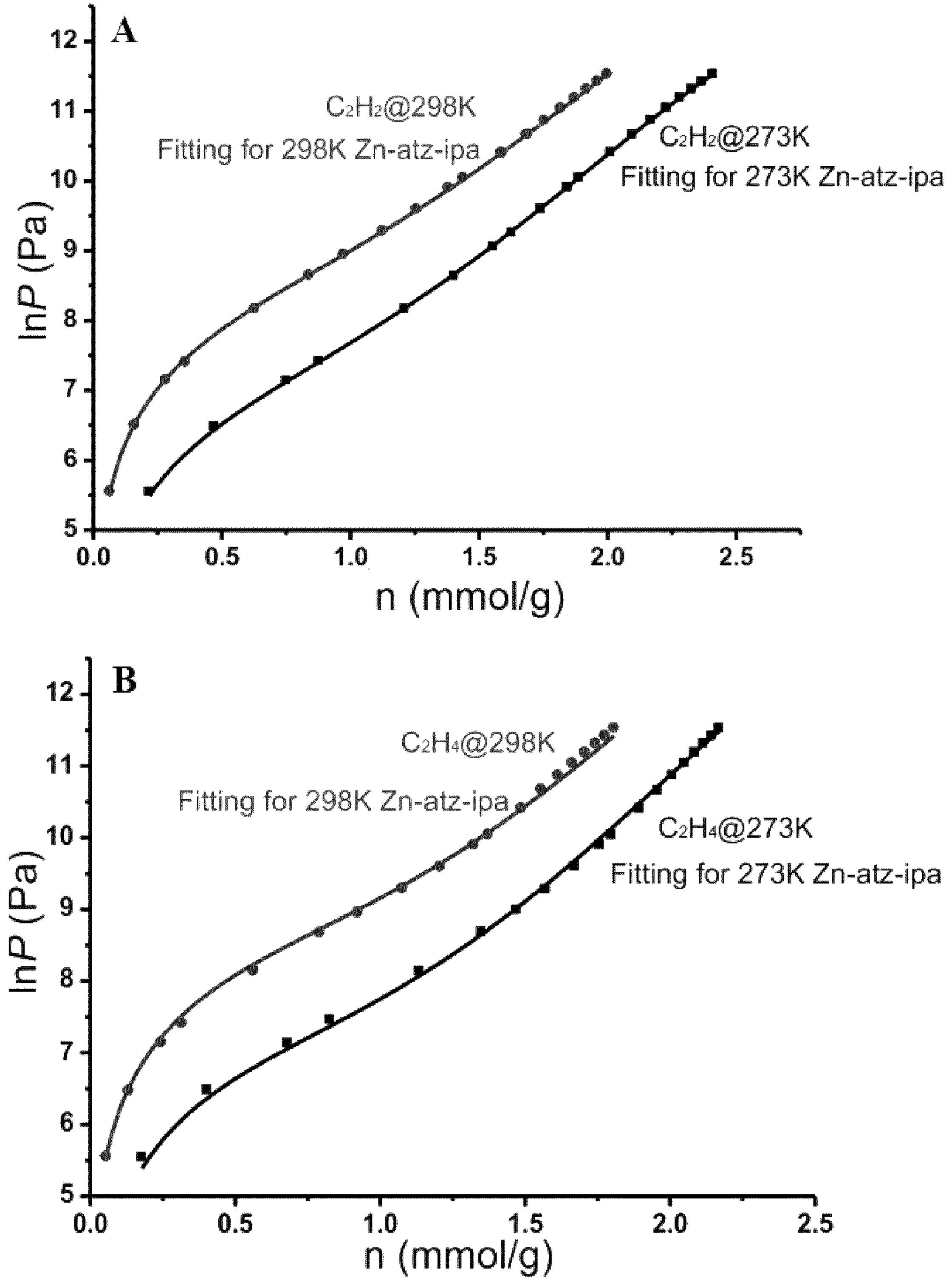
FIG. 8: Graphs showing virial fitting of $C_2H_2$ (FIG. 8, panel A) and $C_2H_4$ (FIG. 8, panel B) sorption data for Zn-atz-ipa.
Figure 9:
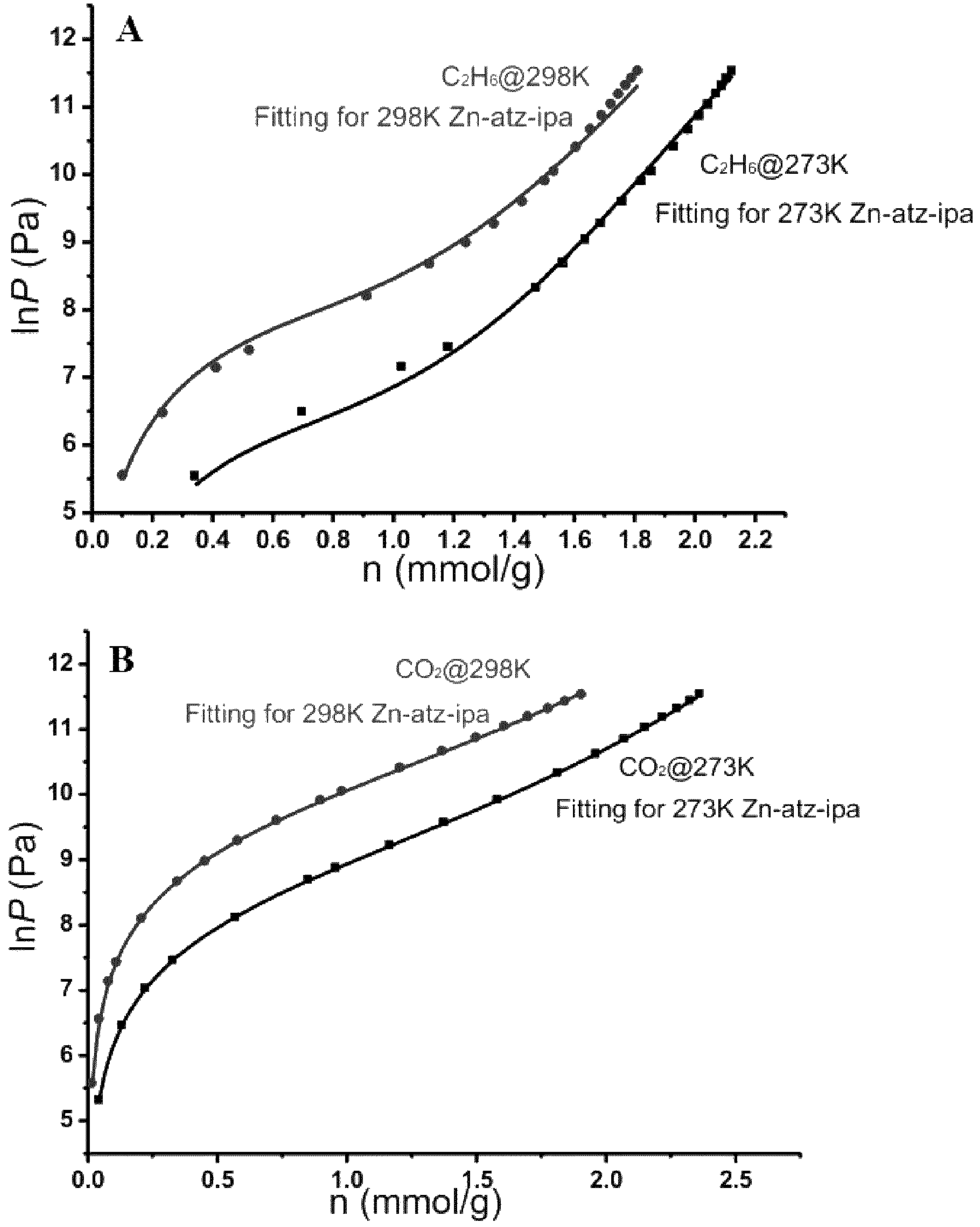
FIG. 9: Graphs showing virial fitting of $C_2H_6$ (FIG. 9, panel A) and $CO_2$ (FIG. 9, panel B) sorption data for Zn-atz-ipa.

Each sorbent was synthesized according to the methods described above. To verify purity, powder X-ray diffraction patterns and sorption data at cryogenic temperatures were performed on as-synthesized materials after activation (as shown in FIGS. 1 and 2). Single-gas isotherms at 273 and 298 K were collected to 1 bar for TIFSIX-2-Cu-i, SIFSIX-3-Ni and Zn-atz-ipa. As revealed by FIG. 3, panel B, at 298 K and 1 bar, TIFSIX-2-Cu-i exhibits less uptake for $C_2H_6$ (2.1 mmol/g) than $C_2H_4$ (2.6 mmol/g), $CO_2$ (4.3 mmol/g) and $C_2H_2$ (4.1 mmol/g). $C_2H_2$ exhibits the highest uptake from 0-0.8 bar for TIFSIX-2-Cu-i. In the case of SIFSIX-3-Ni, $CO_2$ exhibits the highest uptake at 298 K and below 0.2 bar (FIG. 3, panel C). For Zn-atz-ipa, all four gases show very similar uptake (1.8-2.0 mmol/g) at 1 bar and 298 K (FIG. 3, panel A). However, from 0-0.4 bar, higher uptake for $C_2H_6$ vs. $CO_2$, $C_2H_2$ and $C_2H_4$ was measured.

Isotherms at 298K were also collected for Zn-datz-ipa, MET-2, MET-5 and MET-6, as shown in FIGS. 22-25. All of these materials show higher uptake for $C_2H_6$ over $C_2H_2$, $C_2H_4$ and $CO_2$. For the MET materials, $C_2H_6$ uptakes are higher than for other gases over 0-1 bar pressure range. In particular, MET-2 shows a much higher $C_2H_6$ uptake of 1.6 mmol/g at 298 K and 1 bar than $C_2H_4$ of 1.2 mmol/g, $C_2H_2$ of 1.2 mmol/g and $CO_2$ of 1.1 mmol/g.

Figure 10:
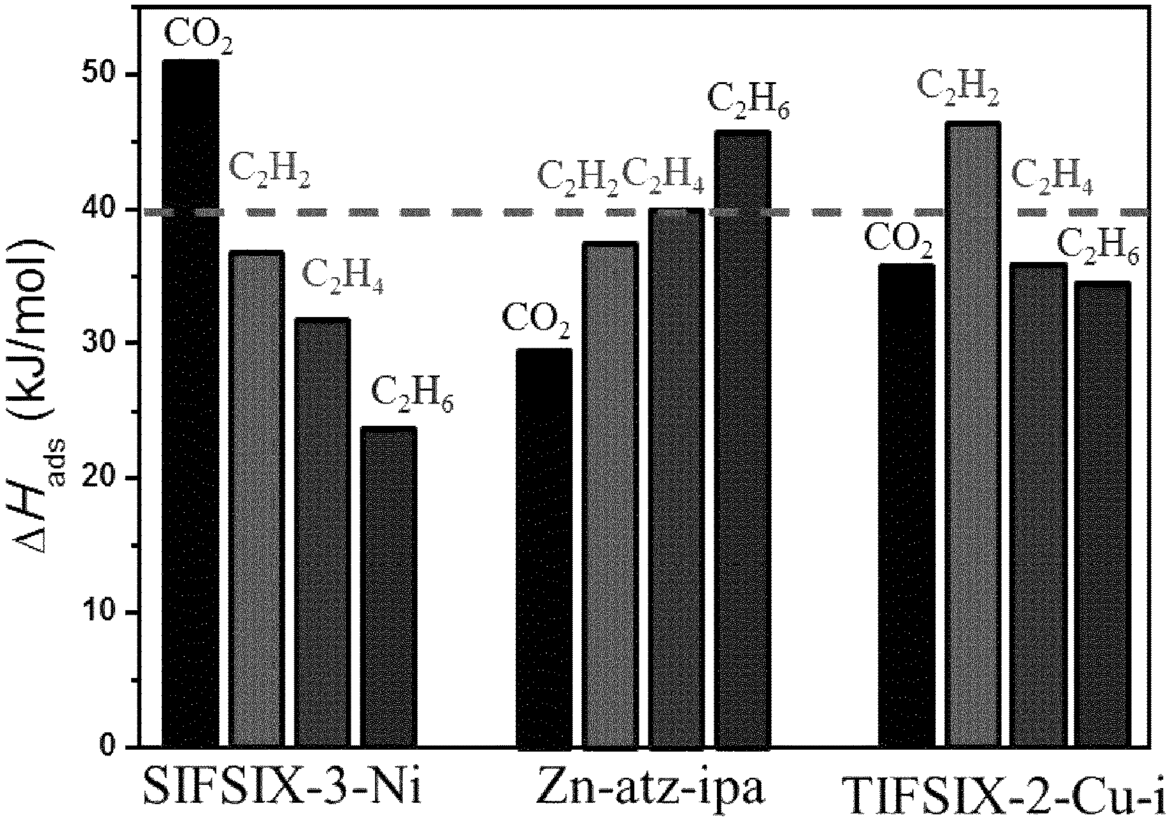
FIG. 10: Graph showing a comparison of isosteric heat of adsorption ($Q_{st}$) values at low loading of $C_2H_2$, $C_2H_4$, $C_2H_6$ and $CO_2$ in TIFSIX-2-Cu-i, SIFSIX-3-Ni and Zn-atz-ipa.
Figure 11:
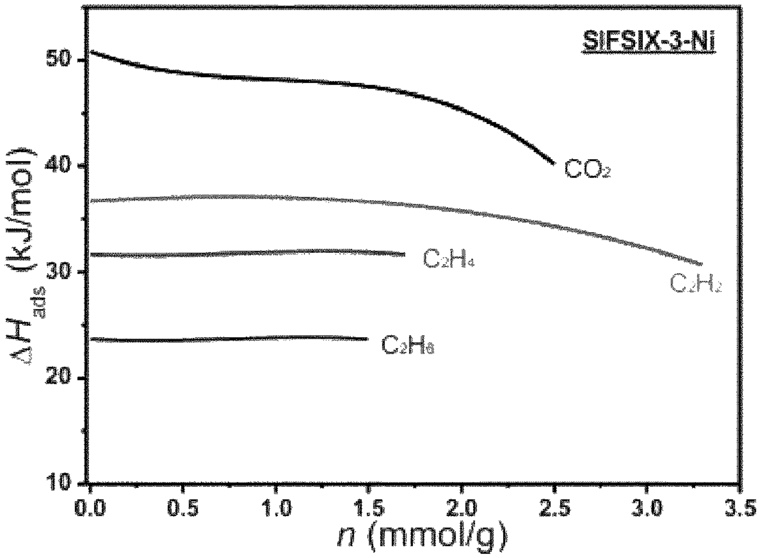
FIG. 11: Graph showing $Q_{st}$ curves for $C_2H_2$, $C_2H_4$, $C_2H_6$ and $CO_2$ in SIFSIX-3-Ni.
Figure 12:
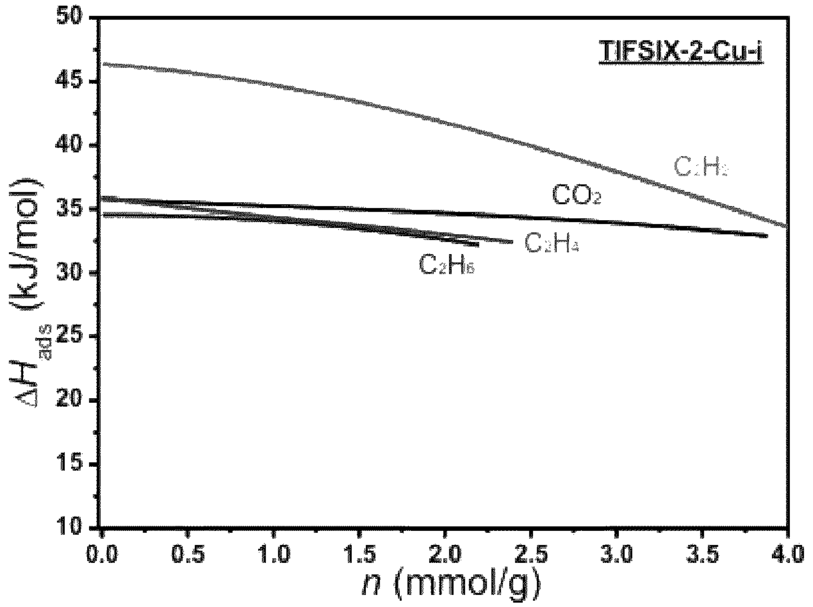
FIG. 12: Graph showing $Q_{st}$ curves for $C_2H_2$, $C_2H_4$, $C_2H_6$ and $CO_2$ in TIFSIX-2-Cu-i.
Figure 13:
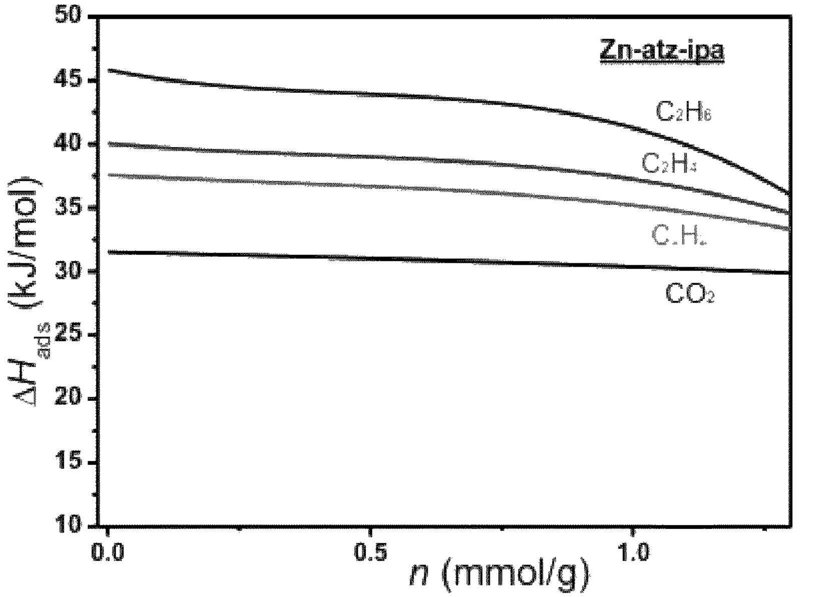
FIG. 13: Graph showing $Q_{st}$ curves for $C_2H_2$, $C_2H_4$, $C_2H_6$ and $CO_2$ in Zn-atz-ipa.

To quantify the interaction strength between each gas and the respective frameworks, 273 and 298 K sorption data were fitted by the virial equation (FIGS. 4 to 9). The isosteric heat of adsorption ($Q_{st}$) was then calculated based on the Clausius—Clapeyron equation. $Q_{st}$ values at low loading of four gases in TIFSIX-2-Cu-i, SIFSIX-3-Ni and Zn-atz-ipa are compared in FIG. 10. Full $Q_{st}$ curves for the four gases in the three ultramicroporous sorbents are given in FIGS. 11 to 13 and summarized in Table 1.

As can be seen in Table 1, each sorbent material exhibits strong selectivity for one gas over the other three according to $Q_{st}$: $CO_2$ for SIFSIX-3-Ni (50.9 kJ/mol), $C_2H_6$ for Zn-atz-ipa (45.8 kJ/mol) and $C_2H_2$ for TIFSIX-2-Cu-i (46.3 kJ/mol) (see dashed line in FIG. 10H). This means that, at least in principle, $CO_2$, $C_2H_2$ and $C_2H_6$ in a four-gas mixture including $C_2H_4$, will be preferably captured in SIFSIX-3-Ni, TIFSIX-2-Cu-i and Zn-atz-ipa, respectively.

Column Breakthrough Experiments

Figure 14:
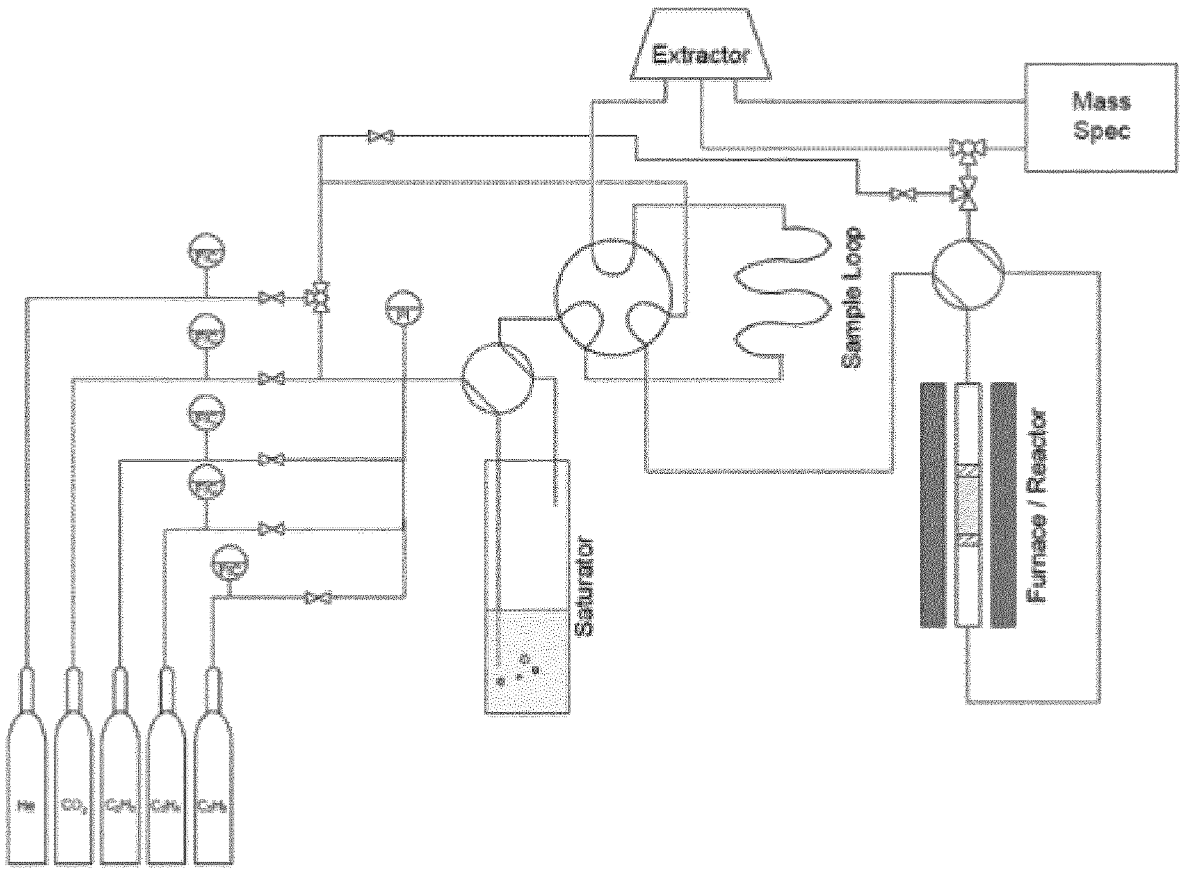
FIG. 14: Schematic diagram of custom-built apparatus for column breakthrough experiments.
Figure 15:
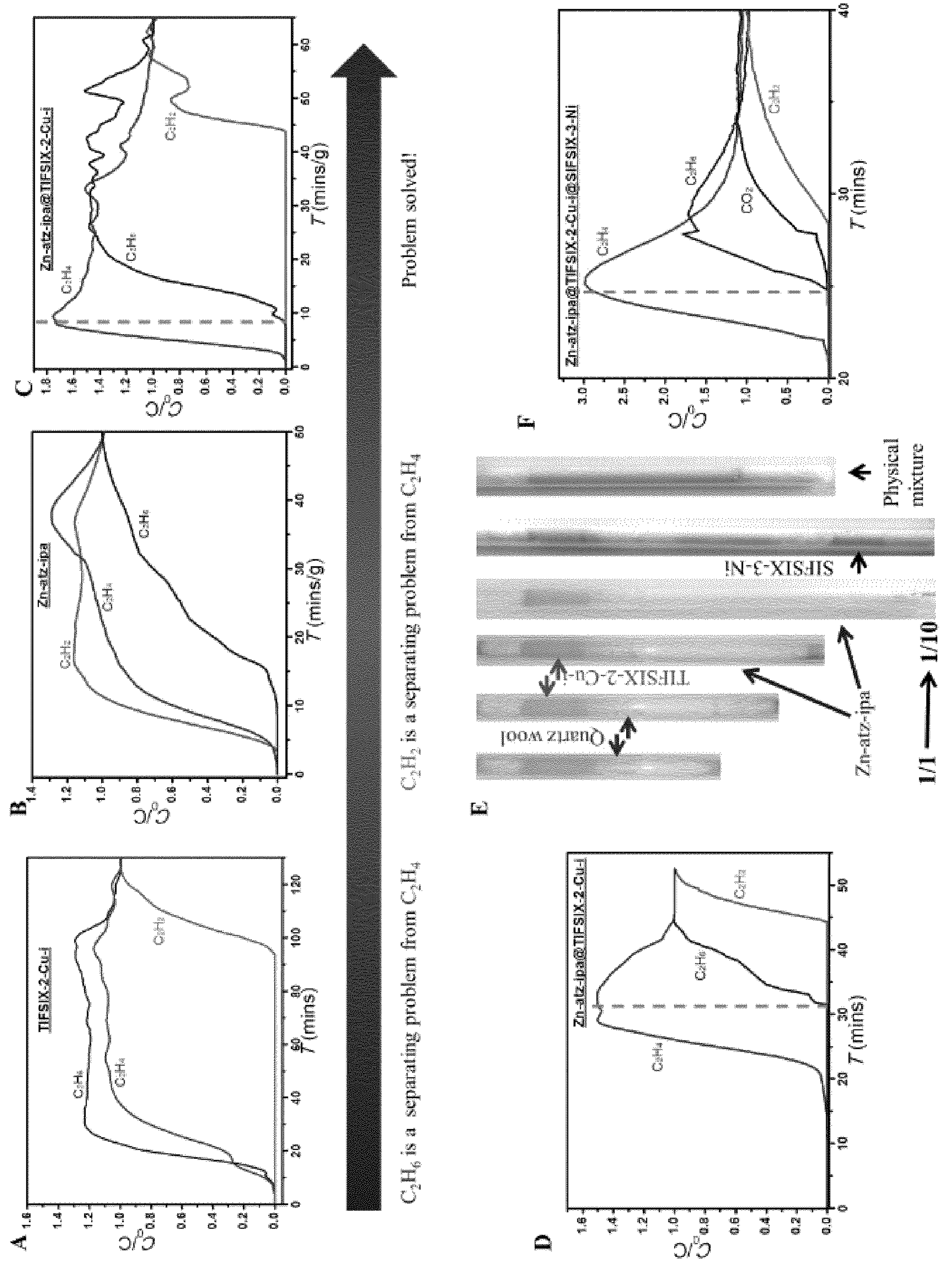
FIG. 15: Graphs showing results of column breakthrough experiments for: an equimolar 3-component gas mixture of $C_2H_2/C_2H_4/C_2H_6$ with a sorbent bed of TIFSIX-2-Cu-i (FIG. 15, panel A), a sorbent bed of Zn-atz-ipa (FIG. 15, panel B) or a $_2$-component (tandem) sorbent bed comprising TIFSIX-2-Cu-i and Zn-atz-ipa (FIG. 15, panel C); a $_3$-component gas mixture of $C_2H_2/C_2H_4/C_2H_6$ (1/49.5/49.5) with a 2-component (tandem) sorbent bed comprising TIFSIX-2-Cu-i and Zn-atz-ipa (FIG. 15, panel D); and an equimolar 4-component gas mixture of $CO_2/C_2H_2/C_2H_4/C_2H_6$ with a 3-component (tandem) sorbent bed comprising TIFSIX-2-Cu-I, Zn-atz-ipa and SIFSIX-3-Ni (FIG. 15, panel F). Photograph showing sorption beds (FIG. 15, panel E).
Figure 16:
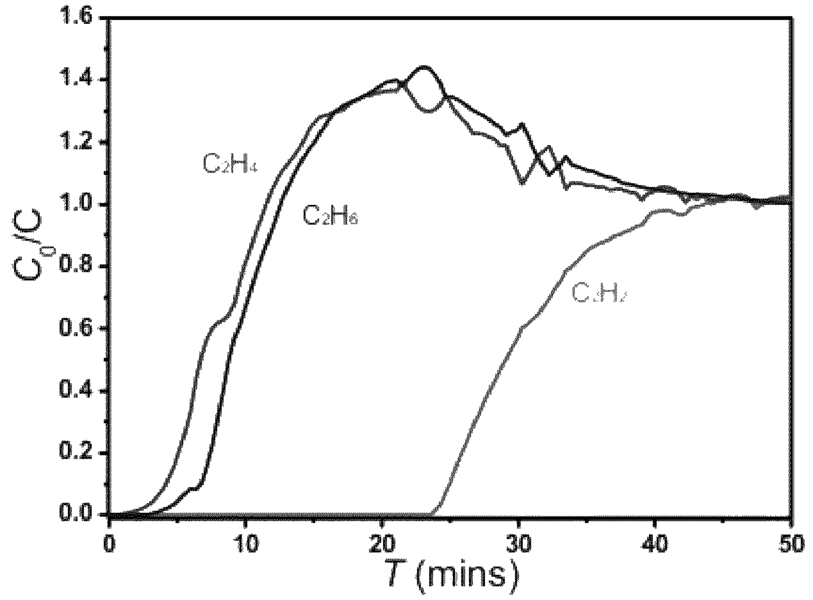
FIGS. 16 to 19: Series of graphs showing column breakthrough results for 2-component sorbent material with increasing mass ratio of Zn-atz-ipa over TIFSIX-2-Cu-i from 1/1 to 10/1.
Figure 17:
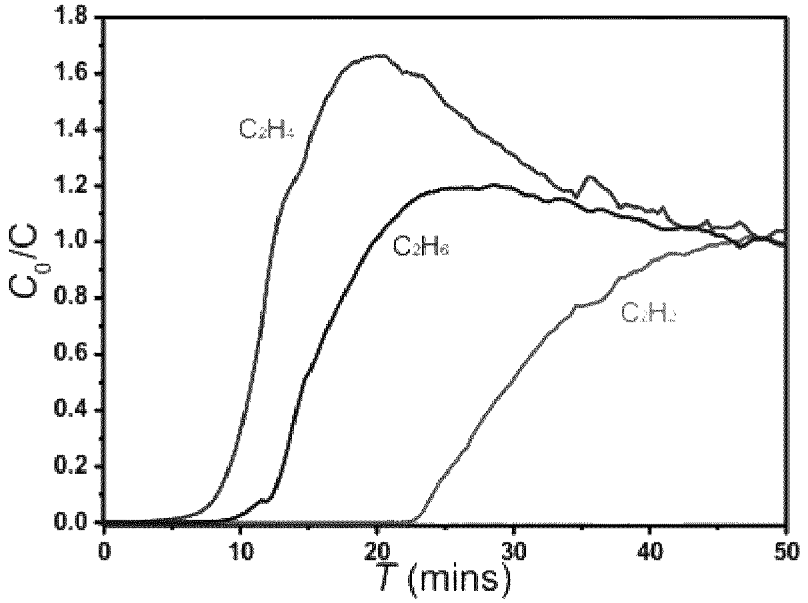
Figure 18:
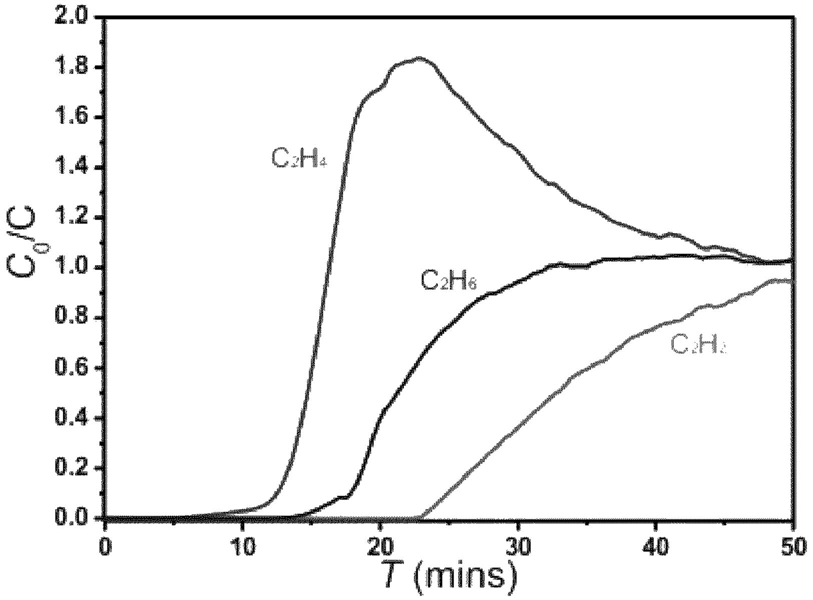
Figure 19:
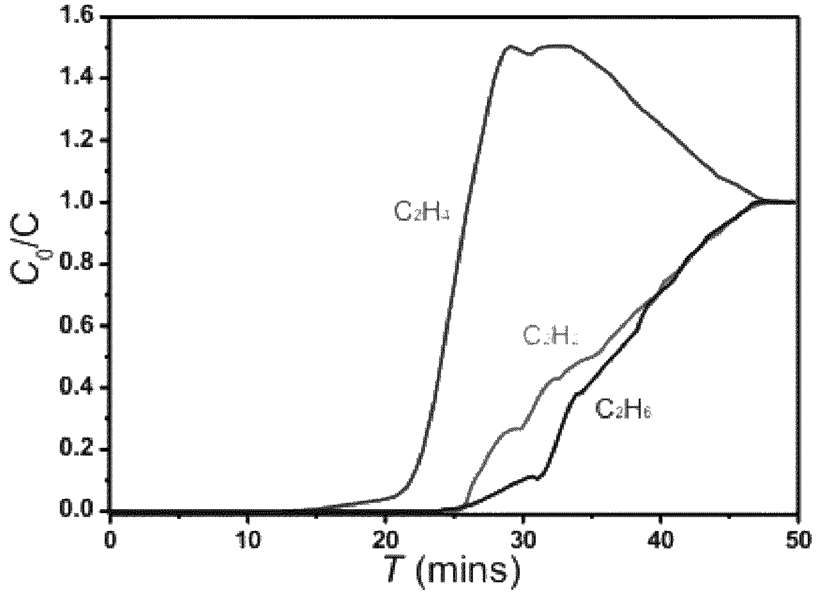

Dynamic breakthrough experiments at 298 K were conducted on a custom-built apparatus (FIG. 14) using an equimolar 3-component gas mixture of $C_2H_2/C_2H_4/C_2H_6$ and a total pressure of 1 bar. Control experiments using sorbent beds filled solely with TIFSIX-2-Cu-i and Zn-atz-ipa were performed. $C_2H_2$ was selectively captured, but $C_2H_4$ and $C_2H_6$ were not separated by TIFSIX-2-Cu-i (FIG. 15, panel A). For Zn-atz-ipa, a similar problem occurred (FIG. 15, panel B), but for $C_2H_2/C_2H_4$, $C_2H_6$ was selectively adsorbed for ca. 10 minutes before breakthrough. However, a 2-component (tandem) sorbent bed comprising TIFSIX-2-Cu-i and Zn-atz-ipa, cleanly removed both $C_2H_2$ and $C_2H_6$ with $C_2H_4$ at >99.9% purity in the effluent stream (FIG. 15, panel C).

By increasing the mass ratio of Zn-atz-ipa over TIFSIX-2-Cu-i from 1/1 to 10/1, breakthrough times of $C_2H_2$ and $C_2H_6$ were optimized for the production of pure $C_2H_4$ using the 2-component sorbent material (FIG. 15, panel E and FIGS. 16 to 19). In the case of the 10/1 ratio, $C_2H_2$ and $C_2H_6$ were observed to breakthrough simultaneously, suggesting that the adsorption capacities of the two adsorbents had been fully utilized.

Figure 20:
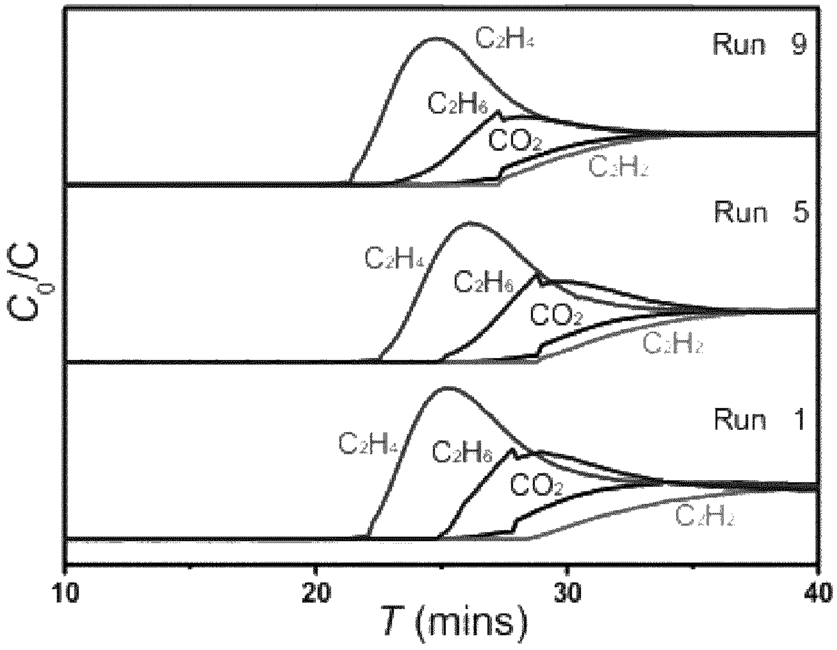
FIG. 20: Graph showing column breakthrough results for sorbent recycling tests.
Figure 21:
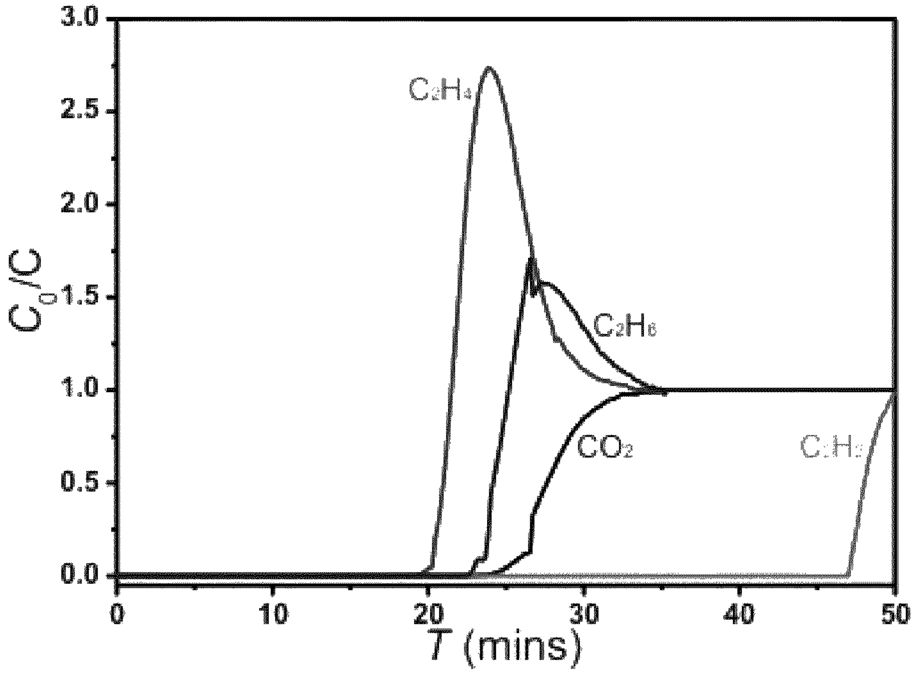
FIG. 21: Graph showing column breakthrough results for a 4-component gas mixture of $CO_2/C_2H_2/C_2H_4/C_2H_6$ (1/33/33/33).
Figure 22:
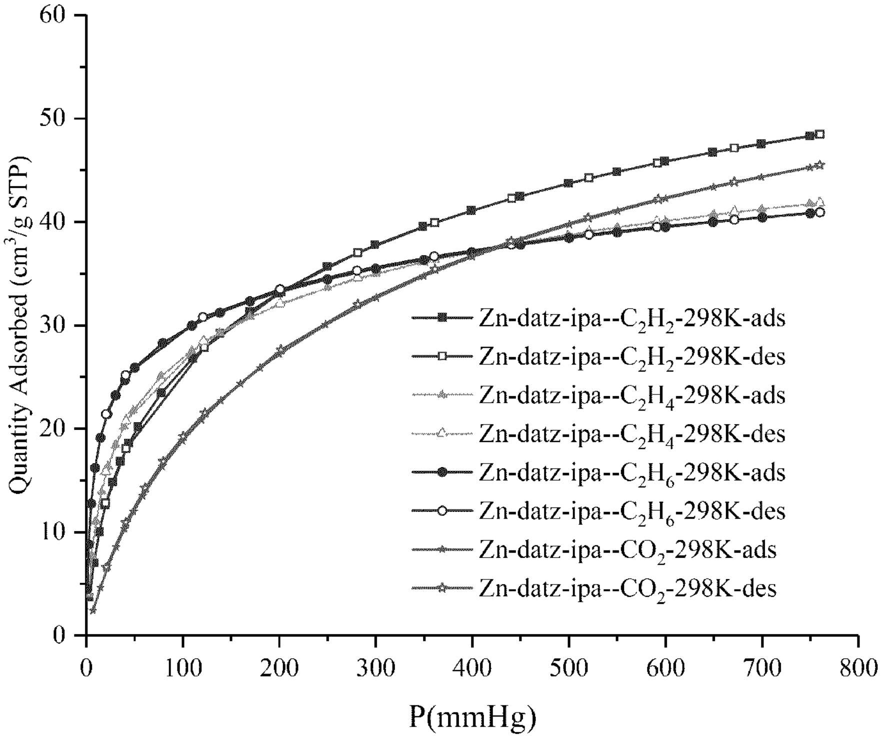
FIG. 22: Graph showing isotherms at 298K collected for Zn-datz-ipa.
Figure 23:
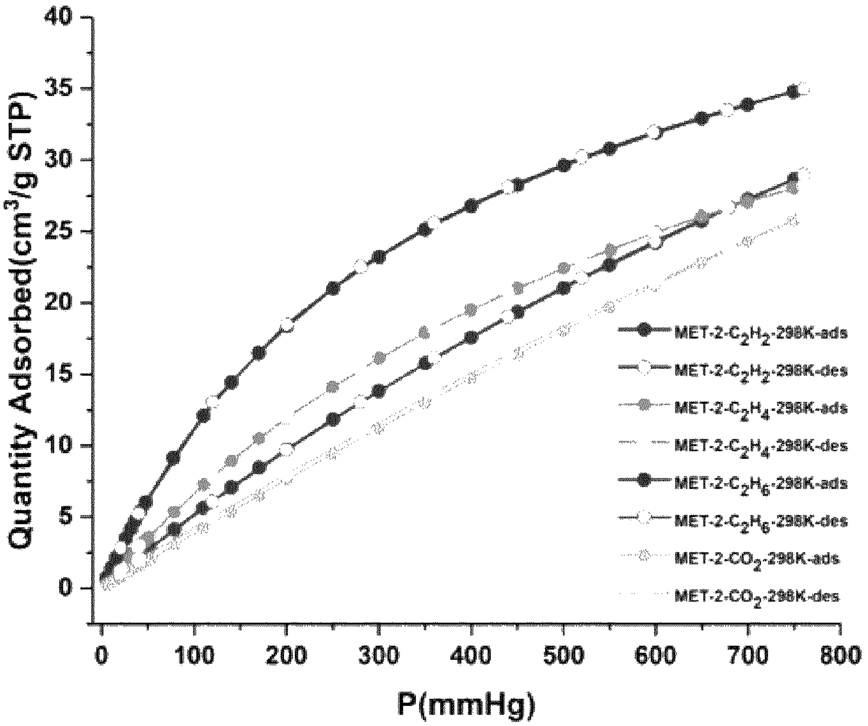
FIG. 23: Graph showing isotherms at 298K collected for MET-2.
Figure 24:
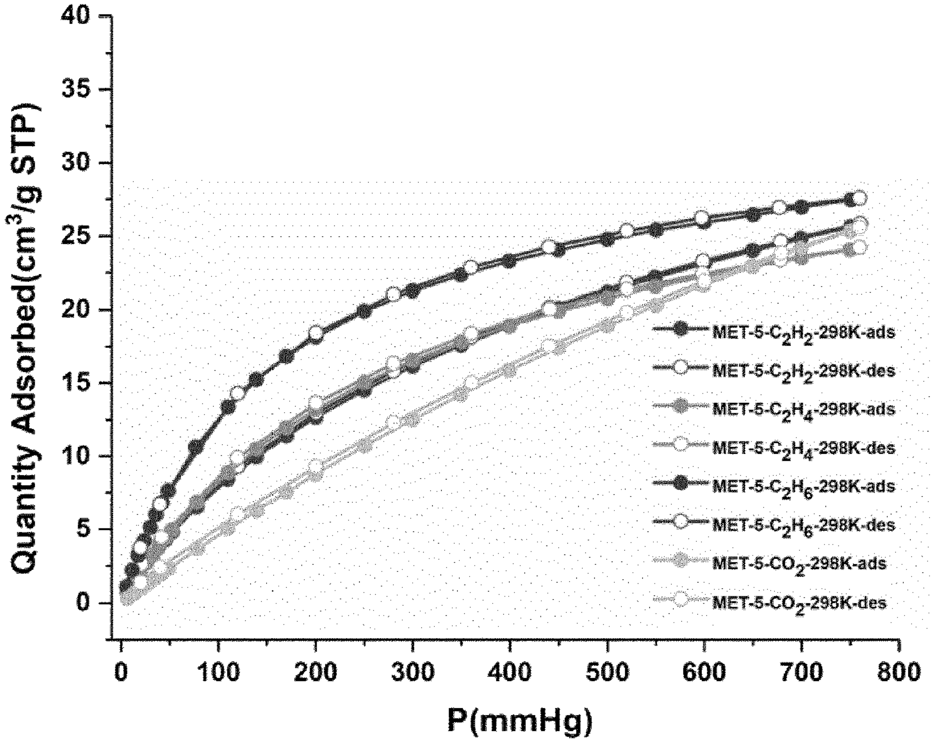
FIG. 24: Graph showing isotherms at 298K collected for MET-5.
Figure 25:
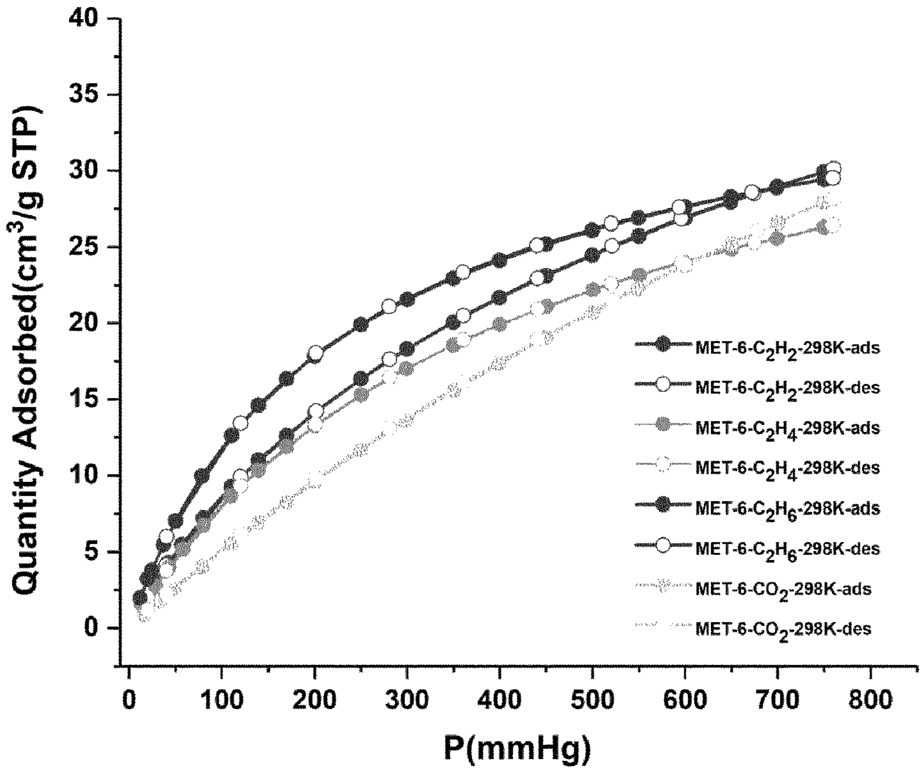
FIG. 25: Graph showing isotherms at 298K collected for MET-6.

The 4-component equimolar mixture of $C_2H_2/C_2H_4/C_2H_6/CO_2$ was studied after adding SIFSIX-3-Ni to make a 3-component sorbent bed. After comparing the $CO_2$ uptake of SIFSIX-3-Ni with those of $C_2H_2$ and $C_2H_6$ in the single-gas adsorption studies, a ratio of 1/1.25/10 (TIFSIX-2-Cu-i: 120 mg; SIFSIX-3-Ni: 150 mg; Zn-atz-ipa: 1.2 g) was adopted. Breakthrough results reveal that $CO_2$, $C_2H_6$ and $C_2H_2$ were captured (FIG. 15, panel F) as polymer-grade $C_2H_4$ was harvested in the effluent stream (working capacity 0.14 mmol/g). After regeneration (<60° C.) under He gas flow (10 ml/min, 1 hour), the sorbent bed was reused; performance was unaffected after 9 such cycles (FIG. 20).

Sorbent recycling tests for each adsorbent (i.e. $CO_2$ for SIFSIX-3-Ni, $C_2H_2$ for TIFSIX-2-Cu-i and $C_2H_6$ for Zn-atz-ipa) were conducted in order to verify ease of recyclability and revealed no capacity loss after 10 cycles. To address the energy footprint of the SSST columns, temperature pro

TABLE 1

| | | 298 K uptake[b] | | | | Low loading $Q_{st}$[c] | | | | | | |
|---|---|---|---|---|---|---|---|---|---|---|---|---|
| | $S_{BET}$[a] | $C_2H_2$ | $C_2H_4$ | $C_2H_6$ | $CO_2$ | $C_2H_2$ | $C_2H_4$ | $C_2H_6$ | $CO_2$ | IAST selectivity[d] | | |
| | | | | | | | | | | $CO_2/C_2H_2$ | $CO_2/C_2H_4$ | $CO_2/C_2H_6$ |
| SIFSIX-3-Ni | 230 | 2.73/3.59 | 0.52/1.98 | 0.32/1.53 | 2.60/2.70 | 36.7 | 31.7 | 23.7 | 50.9 | 6.9 | 103 | 308 |
| | | | | | | | | | | $C_2H_2/C_2H_4$ | $C_2H_2/C_2H_6$ | $C_2H_2/CO_2$ |
| TIFSIX-2-Cu-i | 685 | 3.69/4.38 | 1.47/2.75 | 1.0/2.2 | 2.60/4.27 | 46.3 | 35.9 | 34.5 | 35.8 | 48.8 | 97.8 | 6.1 |
| | | | | | | | | | | $C_2H_6/C_2H_2$ | $C_2H_6/C_2H_4$ | $C_2H_6/CO_2$ |
| Zn-atz-ipa | 650 | 1.43/1.99 | 1.37/1.80 | 1.53/1.81 | 0.98/1.90 | 37.5 | 40.0 | 45.8 | 31.5 | 2 | 1.7 | 5 |

[a]calculated from 77 K $N_2$ and 273 K $CO_2$ sorption ($m^2$/g);

[b]uptake at 0.25/1 bar and 298K (mmol/g);

[c]$Q_{st}$ at zero loading (kJ/mol);

[d]calculated at 298 K and 1 bar of total pressure from binary gas mixture with 1:1 ratio.

grammed desorption (TPD) experiments were conducted for each individual adsorbent and all tandem packed columns after four-gas mixture breakthroughs. Sorbent bed regeneration was achieved with a regeneration temperature of only 60° C. This low regeneration temperature fulfils the promise offered by physisorbents.

TABLE 2

| Packing order | Time for removal after breakthrough[a] (mins) $C_2H_2$ | $C_2H_4$ | $C_2H_6$ | $CO_2$ | Regeneration condition |
|---|---|---|---|---|---|
| A-C-B | 44.6 | 48.3 | 30.9 | 73.0 | 60° C., He (20 ml/min) |
| B-C-A | 46.4 | 48.9 | 31.5 | 93.2 | 60° C., He (20 ml/min) |
| A-B-C | 81.2 | 81.6 | 47.7 | 78.8 | 60° C., He (20 ml/min) |
| C-B-A | 75.1 | 80.1 | 41.1 | 90.0 | 60° C., He (20 ml/min) |
| B-A-C | 75.3 | 60.2 | 40.9 | 80.0 | 60° C., He (20 ml/min) |
| C-A-B | 44.7 | 44.5 | 43.1 | 49.2 | 60° C., He (20 ml/min) |
| A | 22.5 | 28.3 | 23.7 | 49.4 | 60° C., He (20 ml/min) |
| B | 66.8 | 71.7 | 26.5 | 30.3 | 60° C., He (20 ml/min) |
| C | 30.4 | 46.2 | 35.6 | 29.7 | 60° C., He (20 ml/min) |

| Single adsorbent | Run[b] 1 | 2 | 3 | 4 | 5 | 6 | 7 | 8 | 9 | Regeneration condition |
|---|---|---|---|---|---|---|---|---|---|---|
| A-$CO_2$ | 109.7 | 109.7 | 109.7 | 109.6 | 109.6 | 109.5 | 109.6 | 109.6 | 109.7 | 60° C., $N_2$ (20 ml/min) |
| B-$C_2H_2$ | 108.0 | 108.1 | 108.2 | 108.3 | 108.2 | 108.2 | 108.0 | 108.0 | 108.1 | 60° C., $N_2$ (20 ml/min) |
| C-$C_2H_6$ | 104.7 | 104.7 | 104.6 | 104.6 | 104.5 | 104.5 | 104.5 | 104.5 | 104.4 | 60° C., $N_2$ (20 ml/min) |

A: SIFSIX-3-Ni;
B: TIFSIX-2-Cu-i;
C: Zn-atz-ipa a: Ending time (mins) for each gas releasing from post-breakthrough column under regeneration condition, is considered as the time at which the outlet concentration reaches less than 1% of initial concentration; b: Uptake (weight percentages of saturated adsorbent, assuming the activated adsorbent as 100%) for each adsorbent at the end of each adsorption cycle (adsorption at 30° C. under corresponding gas flow), whereas desorption follows at 60° C. under $N_2$ flow.

In industrial $C_2$ hydrocarbon gas streams, acetylene typically makes up only around 1 wt % of the total flow. In order to examine the performance of the sorbent materials with more industrially relevant and challenging gas mixtures, $C_2H_2/C_2H_4/C_2H_6$ (1/49.5/49.5) and $C_2H_2/C_2H_4/C_2H_6/CO_2$ (1/33/33/33) were tested.

Polymer-grade $C_2H_4$ with working capacities of 0.32 and 0.10 mmol/g was harvested from gas mixtures of 1/49.5/49.5 and 1/33/33/33, respectively (FIGS. 15, panel D and 21). The higher partial pressure of $C_2H_6$ in the 1/49.5/49.5 gas mixture contributes to the higher working capacity for $C_2H_4$ production with more $C_2H_6$ molecules being captured at higher partial pressures (0.495 vs 0.33 bar) by Zn-atz-ipa. 0.33 bar) by Zn-atz-ipa.

To explore how performance is affected by packing in a combination sorbent bed, we mixed 120 mg of TIFSIX-2-Cu-i and 1200 mg of Zn-atz-ipa to generate a physical mixture and tested its performance. Breakthrough data for an equimolar gas mixture of $C_2H_2/C_2H_4/C_2H_6$ reveals that $C_2H_2$ was not effectively removed before $C_2H_4$ breakthrough. Further, the $C_2H_6$ concentration was not reduced to the required specification (i.e. <0.1%).

The effect of packing order on performance was assessed with six parallel columns and breakthrough experiments using a 1/1/1/1 gas mixture at 298 K and 1 bar. The results showed that with the sorbents arranged in sequence in the following order (with respect to the flow of the gaseous composition) SIFSIX-3-Ni:Zn-atz-ipa:TIFSIX-2-Cu-i, the highest working capacity was obtained (0.14 mmol/g). Generally, improved purifications were obtained when the Zn-atz-ipa was used as the first or second sorbent. The effects of different selectivity values, kinetics and co-adsorption are likely to be the cause of this observation. Particle size and amount of sorbent used was found to have little effect, with smaller particle size and larger sample amounts resulting in a slightly improved $C_2H_4$ purification. Columns with tighter packing provided improved performance.

Further Examples

Synthesis of $[Ni_2(bpy)_2(L\text{-}tart)F_2]$—an Alternative $C_2H_2$ Selective Sorbent to TIFSIX-2-Cu-i L-tartaric acid (31 mg, 0.2 mmol), $NiF_2{\cdot}4H_2O$ (67 mg, 0.4 mmol), LiF (37 mg, 1.5 mmol) and 4,4'-bipyridine (60 mg, 0.4 mmol) were mixed in $H_2O$ (10 mL). This reaction mixture was capped in a 22 mL borosilicate vial and heated at 120° C. for 24 hours. After heating, the mixture was filtered and washed with water, the green powder was harvested. Yield: 77 mg.

Figure 26:
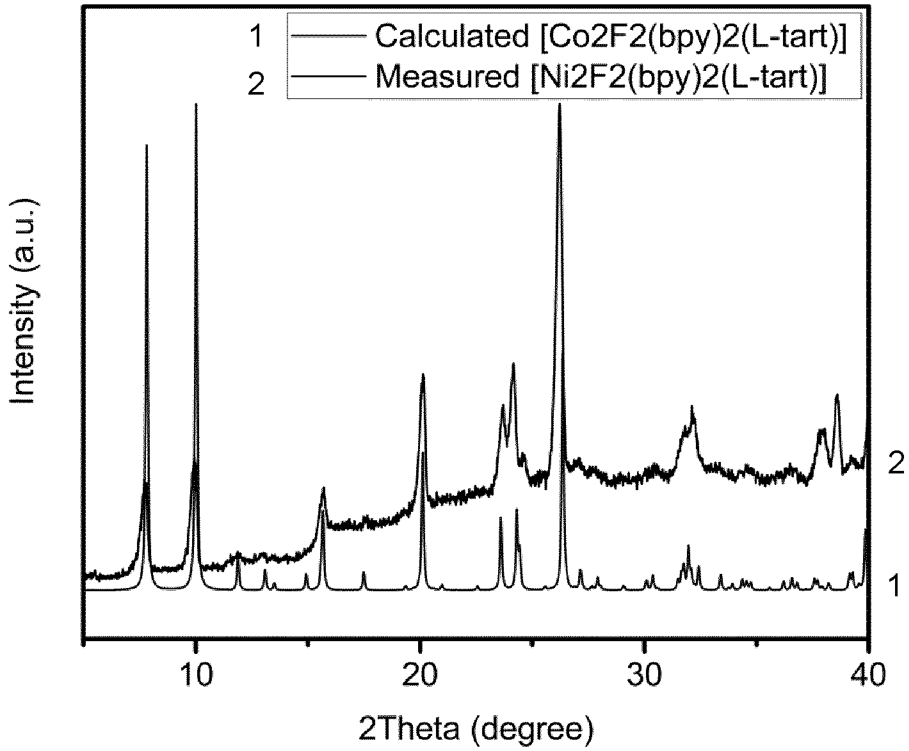
FIG. 26: Calculated powder X-ray powder diffraction pattern of $[Co_2F_2(bpy)_2(L\text{-tart})]$ and measured powder X-ray diffraction pattern of as-synthesized $[Ni_2(bpy)_2(L\text{-tart})F_2]$.
Figure 27:
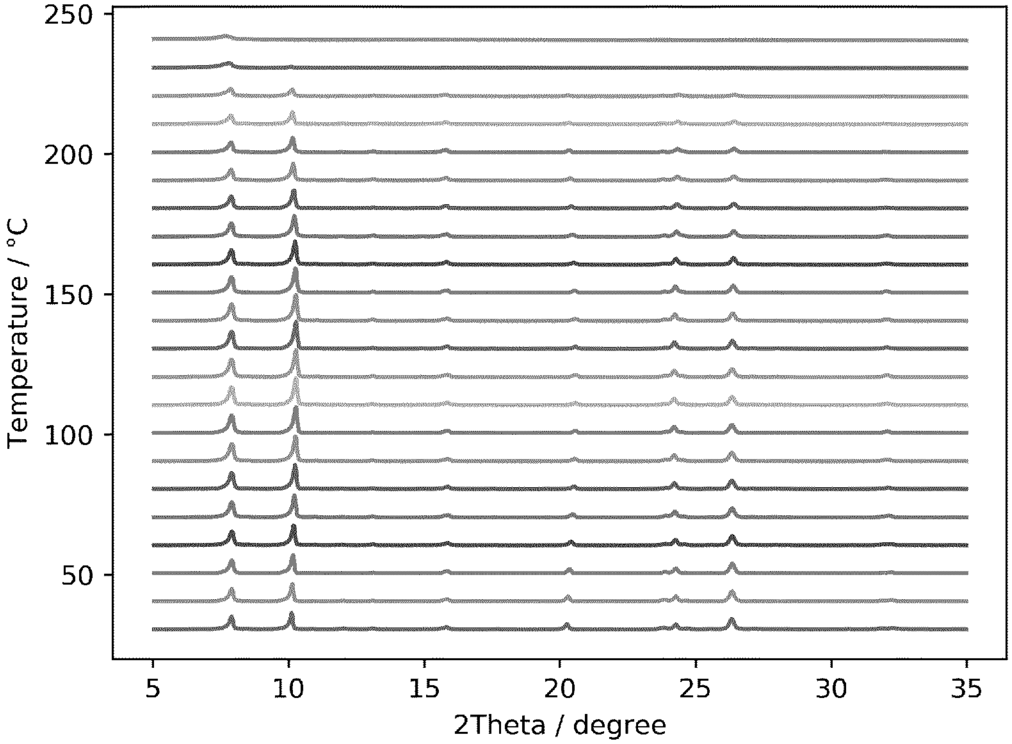
FIG. 27: Variable temperature powder X-ray diffraction patterns of [$Ni_2$(bpy)$_2$(L-tart)$F_2$] measured in nitrogen flow.

Characterization of $[Ni_2(bpy)_2(L\text{-}tart)F_2]$ $[Ni_2(bpy)_2(L\text{-}tart)F_2]$ is isostructural to the $[Co_2F_2(bpy)_2(L\text{-}tart)]$ as previously reported [Zhang, G.; Hu, H.; Li, H.;

Zhao, F.; Liu, Y.; He, X.; Huang, H.; Xu, Y.; Wei, Y.; Kang, Z., Homochiral metal-organic porous materials for enantioselective recognition and electrocatalysis, CrystEngComm 2013, 15(17), 3288-3291]. The phase purity of as-synthesized [$Ni_2$(bpy)$_2$(L-tart)$F_2$] was confirmed by PXRD (FIG. 26). FIG. 26 shows the calculated powder X-ray powder diffraction pattern of [$Co_2F_2$(bpy)$_2$(L-tart)] and measured powder X-ray diffraction pattern of as-synthesized [$Ni_2$(bpy)$_2$(L-tart)$F_2$]. When heated in nitrogen flow, [$Ni_2$(bpy)$_2$(L-tart)$F_2$] maintained crystallinity up to ca. 200° C. (FIG. 27). FIG. 27 shows variable temperature powder X-ray diffraction patterns of [$Ni_2$(bpy)$_2$(L-tart)$F_2$] measured in nitrogen flow.

Sorption Properties of [$Ni_2$(bpy)$_2$(L-tart)$F_2$]

Figure 28:
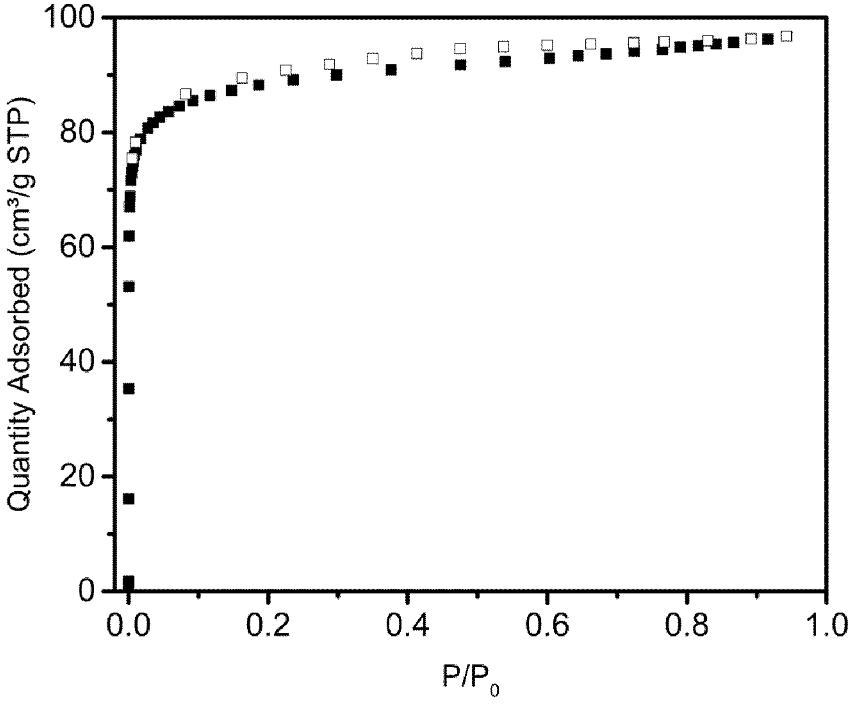
FIG. 28: Graph showing a 77 K $N_2$ sorption isotherm of [$Ni_2$(bpy)$_2$(L-tart)$F_2$].
Figure 29:
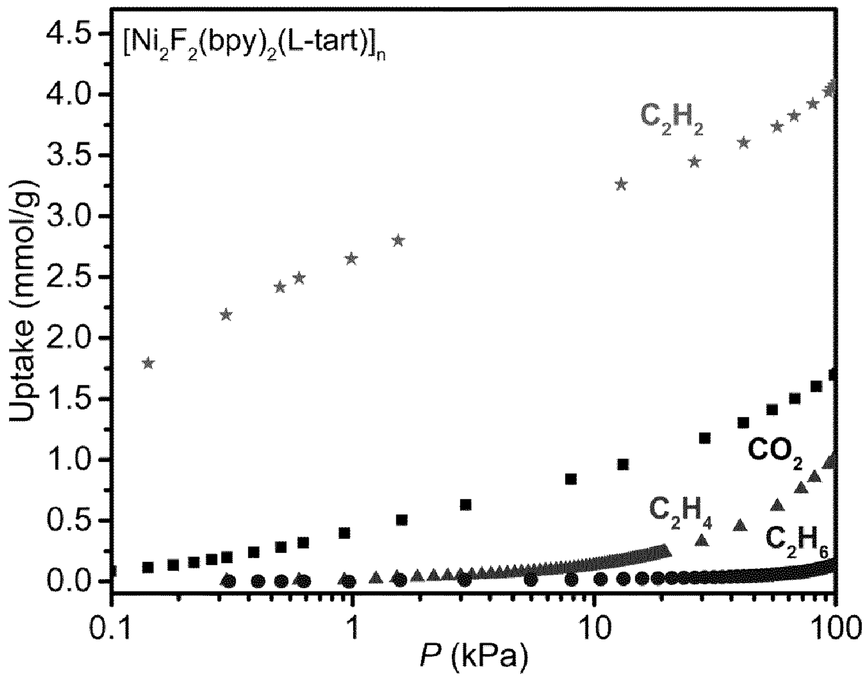
FIG. 29: Graph showing adsorption of $CO_2$ (squares), $C_2H_2$ (stars), $C_2H_4$ (triangles), and $C_2H_6$ (circles) at 298 K for [$Ni_2$(bpy)$_2$(L-tart)$F_2$].

[$Ni_2$(bpy)$_2$(L-tart)$F_2$] exhibits permanent porosity as demonstrated by nitrogen sorption at 77K (FIG. 28). FIG. 28 shows a 77 K $N_2$ sorption isotherm of [$Ni_2$(bpy)$_2$(L-tart)$F_2$]. Single component isotherms collected at 298K on [$Ni_2$(bpy)$_2$(L-tart)$F_2$] demonstrate that the uptake of $C_2H_2$ is higher than the other gases tested (FIG. 29). FIG. 29 shows adsorption of $CO_2$ (squares), $C_2H_2$ (stars), $C_2H_{14}$ (triangles), and $C_2H_6$ (circles) at 298 K for [$Ni_2$(bpy)$_2$(L-tart)$F_2$].

Figure 30:
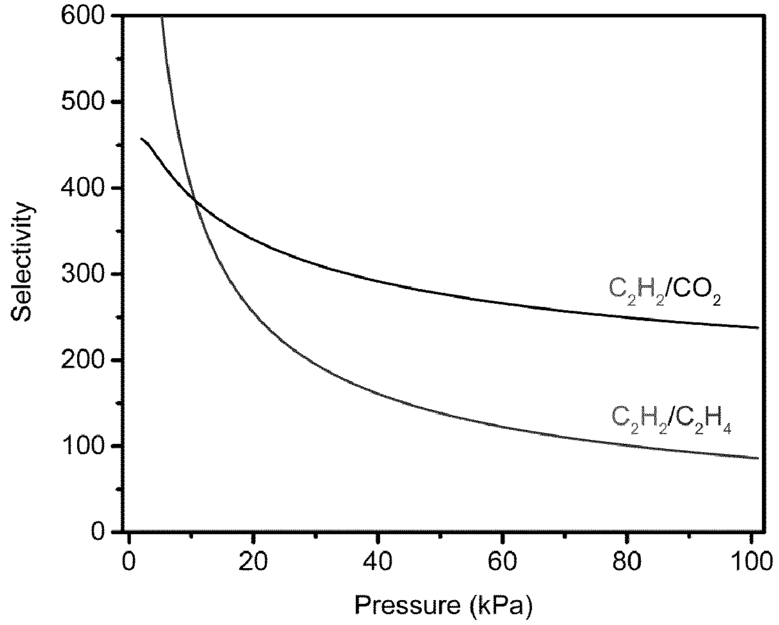
FIG. 30: Graph showino selectivity of $C_2H_2/C_2H_4$, $C_2H_2/C_2H_6$ and $C_2H_2/CO_2$ calculated for equimolar binary mixture at 298 K and 1 bar of total pressure from Ideal Adsorbed Solution Theory (IAST) in [$Ni_2$(bpy)$_2$(L-tart)$F_2$].

A comparison of key sorption parameters of [$Ni_2$(bpy)$_2$(L-tart)$F_2$] and TIFSIX-2-Cu-i can be found in Table 3 and FIG. 30. IAST selectivity calculations indicate that [$Ni_2$(bpy)$_2$(L-tart)$F_2$] can be used as the selective $C_2H_2$ sorbent for SSST and is an alternative to TIFSIX-2-Cu-i. FIG. 30 shows selectivity of $C_2H_2/C_2H_4$, $C_2H_2/C_2H_6$ and $C_2H_2/CO_2$ calculated for equimolar binary mixture at 298 K and 1 bar of total pressure from Ideal Adsorbed Solution Theory (IAST) in [$Ni_2$(bpy)$_2$(L-tart)$F_2$].

TABLE 3

Key sorption parameters of [$Ni_2$(bpy)$_2$(L-tart)$F_2$] and TIFSIX-2-Cu-i.

| | 298 K uptake[a] | | | | IAST selectivity[b] | | |
|---|---|---|---|---|---|---|---|
| | $C_2H_2$ | $C_2H_4$ | $C_2H_6$ | $CO_2$ | $C_2H_2/C_2H_4$ | $C_2H_2/C_2H_6$ | $C_2H_2/CO_2$ |
| TIFSIX-2-Cu-i | 3.69/4.38 | 1.47/2.75 | 1.0/2.2 | 2.60/4.27 | 48.8 | 97.8 | 6.1 |
| [$Ni_2$(bpy)$_2$(L-tart)$F_2$] | 3.44/4.1 | 0.3/1.0 | 0.03/0.14 | 0.17/1.71 | 86 | 10000+ | 237 |

[a]uptake at 0.25/1 bar and 298 K (mmol/g);

[b]calculated at 298 K and 1 bar of total pressure from binary gas mixture with 1:1 ratio.

Synthesis of [$Co_2$(bpy)$_2$(Tzba)$F_2$]—an Alternative $C_2H_6$ Adsorbent to Zn-atz-ipa 4-(1H-Tetrazol-5-yl) benzoic acid (herein referred to as Tbza) (72 mg, 0.38 mmol), 4,4'-bipyridine (47 mg, 0.3 mmol) and $Co(NO_3)_2·6H_2O$ (87 mg, 0.3 mmol) were combined in a mixture of DMF (3 ml), ethanol (6 ml) and $H_2O$ (12 ml) and 6 drops of $HBF_4$. This reaction mixture was then capped in a 22 mL borosilicate vial and heated at 120° C. for 24 hours. After heating, the mixture was filtered and washed with water, the red crystalline powder was harvested. Yield: 65 mg.

Characterization of [$Co_2$(bpy)$_2$(Tzba)$F_2$]

Figure 31:
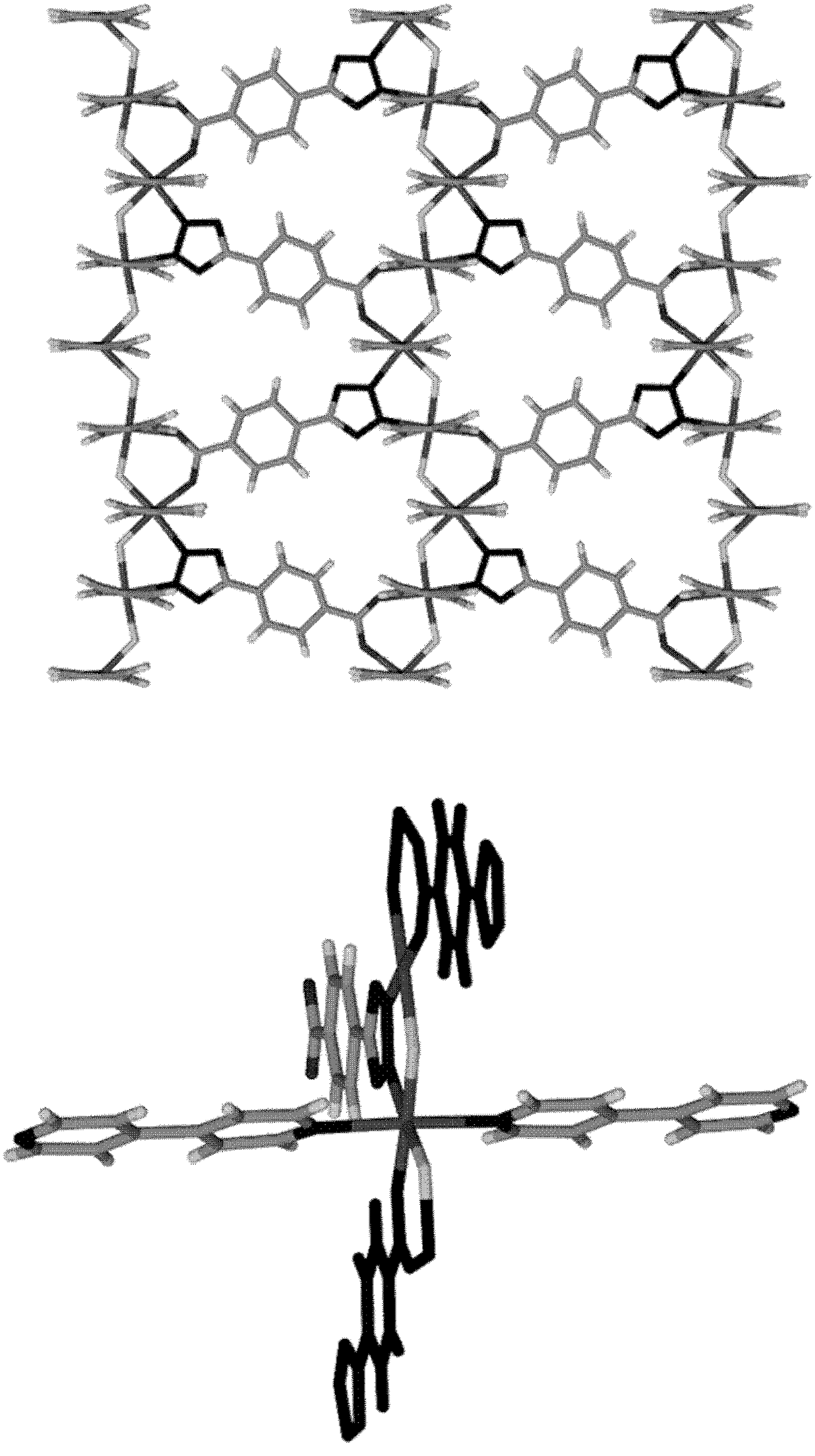
FIG. 31: Diagram showing the coordination environment of [$Co_2$(bpy)$_2$(Tzba)$F_2$] from single crystal data (left) and a packing diagram of [$Co_2$(bpy)$_2$(Tzba)$F_2$] (right). crystal data and measured powder X-ray diffraction patterns of as-synthesized [$Co_2$(bpy)$_2$(Tzba)$F_2$].

The structure of [$Co_2$(bpy)$_2$(Tzba)$F_2$] is illustrated in FIG. 31 and was determined by single crystal X-ray diffraction data collected on a Bruker D8 diffractometer using multilayer monochromated Mo-Kα radiation (λ=0.71073 Å). FIG. 31 shows the coordination environment of [$Co_2$(bpy)$_2$(Tzba)$F_2$] from single crystal data and a packing diagram of [$Co_2$(bpy)$_2$(Tzba)$F_2$]. An Oxford Cryosystems Cryostream 700 Plus was used to maintain the temperature of the crystal at 298 K throughout the data collection. Data reduction was carried out using the Bruker software package SAINT.[1] Absorption corrections and other systematic errors were accounted for using SADABS.[2] The structure was solved by direct methods using SHELXS and refined using SHELXL.[3] X-Seed[4] was used as a graphical interface for the SHELX program suite. Hydrogen atoms were placed in calculated positions using riding models. The coordination environment in [$Co_2$(bpy)$_2$(Tzba)$F_2$] comprises two cobalt metal centres, one TzBa ligand, two bpy ligands and two fluoride anions that bridge neighbouring metal centres. The TzBa ligand chelates two metal centres in an alternating fashion, first through the tetrazole moiety and then through the dicarboxylic acid moiety. This non-interpenetrated 3D MOF contains guest accessible channels of approximately 38% (FIG. 31 right).

Figure 32:
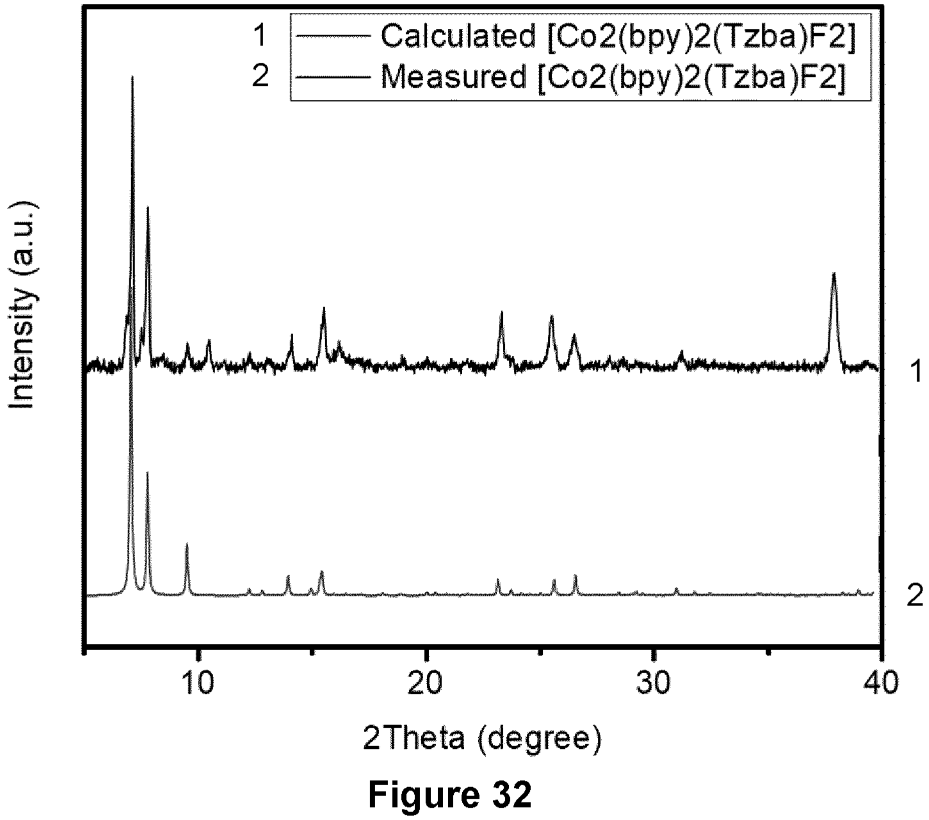
Figure 33:
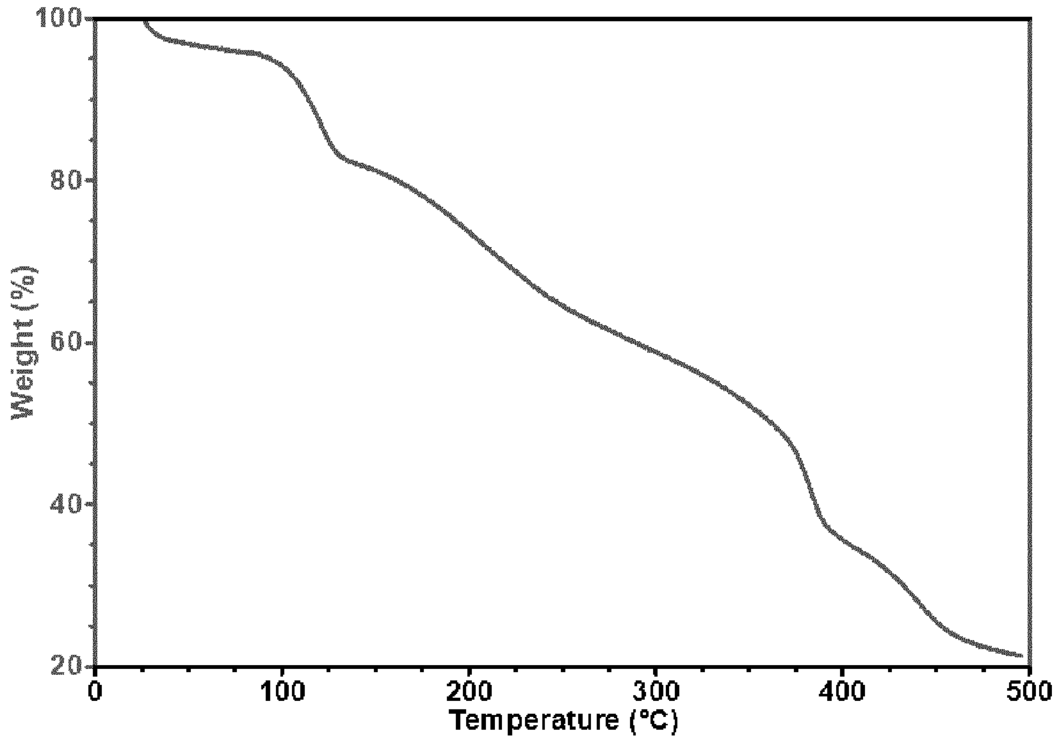
FIG. 33: Graph showing a thermogravimetric analysis trace of [$Co_2$(bpy)$_2$(Tzba)$F_2$] measured under nitrogen flow.

Phase purity of as-synthesized [$Co_2$(bpy)$_2$(Tzba)$F_2$] was confirmed by PXRD (FIG. 32). FIG. 32 shows calculated powder X-ray diffraction patterns of [$Co_2$(bpy)$_2$(Tzba)$F_2$] from single crystal data and measured powder X-ray diffraction patterns of as-synthesized [$Co_2$(bpy)$_2$(Tzba)$F_2$]. When heated under nitrogen flow, [$Co_2$(bpy)$_2$(Tzba)$F_2$] retains crystallinity up to ca. 190° C. (FIG. 33). FIG. 33 shows a thermogravimetric analysis trace of [$Co_2$(bpy)$_2$(Tzba)$F_2$] measured under nitrogen flow.

Sorption Properties of [$Co_2$(bpy)$_2$(Tzba)$F_2$]

Figure 34:
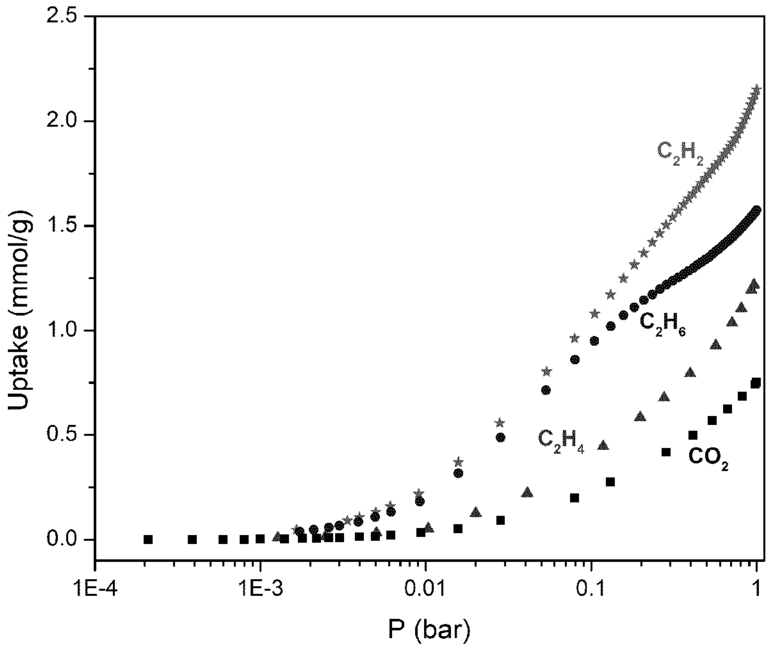
FIG. 34: Graph showing the adsorption of $CO_2$ (squares), $C_2H_2$ (stars), $C_2H_4$ (triangles), and $C_2H_6$ (circles) at 298 K for [$Co_2$(bpy)$_2$(Tzba)$F_2$].
Figure 35:
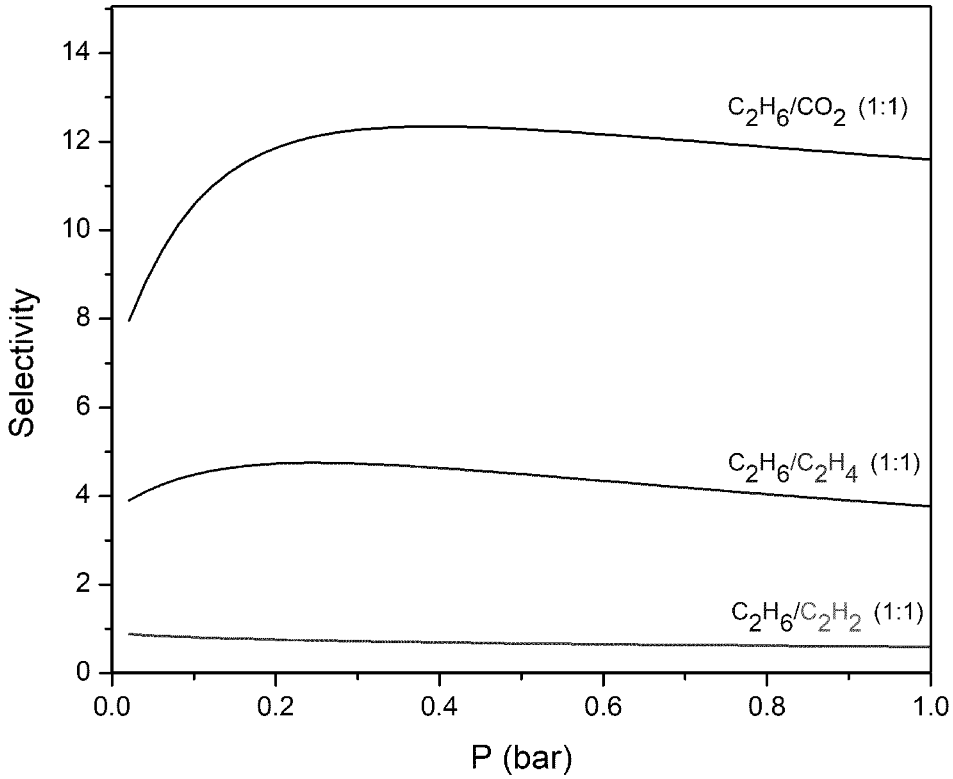
FIG. 35: Graph showing the selectivity of $C_2H_6/C_2H_4$, $C_2H_6/CO_2$ and $C_2H_6/C_2H_2$ calculated for binary mixtures at 298 K and 1 bar of total pressure from IAST in [$Co_2$(bpy)$_2$(Tzba)$F_2$].

[$Co_2$(bpy)$_2$(Tzba)$F_2$] exhibits permanent porosity as demonstrated by sorption of various gases at 298K. Single component isotherms collected at 298K on [$Co_2$(bpy)$_2$(Tzba)$F_2$] demonstrate high preferential $C_2H_6$ uptake vs $C_2H_4$ (FIGS. 34 and 35). FIG. 34 shows the adsorption of $CO_2$ (squares), $C_2H_2$ (stars), $C_2H_4$ (triangles), and $C_2H_6$ (circles) at 298 K for [$Co_2$(bpy)$_2$(Tzba)$F_2$]. FIG. 35 shows the selectivity of $C_2H_6/C_2H_4$, $C_2H_6/CO_2$ and $C_2H_6/C_2H_2$ calculated for binary mixtures at 298 K and 1 bar of total pressure from Ideal Adsorbed Solution Theory (IAST) in [$Co_2$(bpy)$_2$(Tzba)$F_2$].

Comparison of key sorption parameters of [$Co_2$(bpy)$_2$(Tzba)$F_2$] and Zn-atz-ipa are given in Table 5. IAST selectivity calculations indicate that [$Co_2$(bpy)$_2$(Tzba)$F_2$] can be used as the $C_2H_6$ selective sorbent in an SSST process, thus serving an alternative to Zn-atz-ipa.

TABLE 5

Sorption data summary of $[Co_2(bpy)_2(Tzba)F_2]$ and Zn-atz-ipa.

| | 298 K uptake[a] | | | | IAST selectivity[b] | | |
|---|---|---|---|---|---|---|---|
| | $C_2H_2$ | $C_2H_4$ | $C_2H_6$ | $CO_2$ | $C_2H_6/C_2H_4$ | $C_2H_6/C_2H_2$ | $C_2H_6/CO_2$ |
| Zn-atz-ipa | 1.43/1.99 | 1.37/1.80 | 1.53/1.81 | 0.98/1.90 | 1.7 | 2 | 5 |
| $[Co_2(bpy)_2(Tzba)F_2]$ | 1.4/2.1 | 0.7/1.2 | 1.2/1.6 | 2.6/4.2 | 3.8 | 0.6 | 11.6 |

[a]uptake at 0.25/1 bar and 298 K (mmol/g);
[b]calculated at 298 K and 1 bar of total pressure from equimolar binary gas mixtures.

REFERENCES

1. SAINT Data Reduction Software, Version 6.45; Bruker AXS Inc., Madison, Wisc., 2003.
2. (a) SADABS, Version 2.05; Bruker AXS Inc., Madison, Wisc., 2002; (b) Blessing, R. H. An Empirical Correction for Absorption Anisotropy. *Acta Cryst.* 1995, A51, 33-38.
3. Sheldrick, G. M. A Short History of SHELX. *Acta Cryst.* 2008, A64, 112-122.
4. Barbour, L. J. X-Seed—A Software Tool for Supramolecular Crystallography. *J. Supramol. Chem.* 2001, 1, 189-191.

In summary, the present invention provides a single-step method of obtaining a target gas, such as ethylene, methane, propane or propylene, from a gaseous mixture by contacting the gaseous mixture with a sorbent media containing a sorbent media adapted for removal of each gaseous impurity in the gaseous mixture. In particular, the sorbent media of the present invention comprising the sorbent materials described herein provides a one-step $C_2H_4$ purification. Polymer-grade $C_2H_4$ was produced in one-step from tertiary ($C_2H_2/C_2H_4/C_2H_6$) and quaternary ($C_2H_2/C_2H_4/C_2H_6/CO_2$) gas mixtures which mimic those currently produced in industrial processes which are currently separated using multi-step energy intensive methods.

The invention claimed is:

1. A method of obtaining a target gas from a gaseous composition comprising the target gas, a first gas and a second gas, the method comprising the step of contacting the gaseous composition with a sorbent media to remove at least some of the first gas and at least some of the second gas from the gaseous composition; wherein the sorbent media comprises a first sorbent material and a second sorbent material; wherein the sorbent media comprises the first and second sorbent materials, and any further sorbent materials, in discrete sections arranged in series; wherein the first sorbent material is an ultramicroporous material comprising a metal organic material, a metal organic framework material, or a porous coordination polymer material and having pores of an average diameter of less than 0.7 nm and has a higher adsorption selectivity for the first gas than for the target gas; wherein the second sorbent material is an ultramicroporous material comprising a metal organic material, a metal organic framework material, or a porous coordination polymer material and having pores of an average diameter of less than 0.7 nm and has a higher adsorption selectivity for the second gas than for target gas; wherein the target gas is a $C_{1-4}$ hydrocarbon; and wherein the second gas is ethane.

2. The method according to claim 1, wherein the target gas is ethylene, propylene, propane or methane.

3. The method according to claim 1, wherein the first gas is acetylene.

4. The method according to claim 1 wherein the first sorbent material is an ultramicroporous material having a three-dimensional lattice of metal species (M) and linker groups; wherein the metal species (M) are linked together in a first and second dimension by first linker groups ($L^1$) and are linked together in a third dimension by second linker groups ($L^2$) to form the three-dimensional lattice; and wherein one of $L^1$ and $L^2$ is an organic linker group and the other of $L^1$ and $L^2$ is either an inorganic or an organic linker group; and wherein the ultramicroporous material has the formula $M_x(L^1)_2(L^2)Y_z$ wherein x=1 to 3, Y is an inorganic anion and z=0 to 3.

5. The method according to claim 4, wherein Mis $Cu^{2+}$, $L^1$ is 4,4'-bipyridylacetylene and $L^2$ is $TiF_6^{2-}$.

6. The method according to claim 4, wherein M is $Ni^{2+}$, $L^1$ is 4,4'-bipyridine and $L^2$ is tartaric acid.

7. The method according to claim 1, wherein the second sorbent material is an ultramicroporous material of formula $Zn_2(A)_2(B)$; wherein A is an amino-substituted heterocyclic ligand and B is a dicarboxylate ligand.

8. The method according to claim 7, wherein A is an ion derived from 3-amino-1,2,4-triazole and B is an ion derived from isophthalic acid.

9. The method according to claim 1, wherein the second sorbent material is an ultramicroporous material of formula $M_x(L^1)_2(L^2)Y_z$ wherein M is $Co^{2+}$ or $Ni^{2+}$, wherein x is an integer from 1 to 3, $L^1$ is an organic linker group, $L^2$ is a di-carboxylic acid linker or a di-carboxylic acid equivalent linker having an azolate group, Y is an inorganic anion and z is an integer from 0 to 3.

10. The method according to claim 1, wherein the gaseous composition comprises a third gas, as an impurity; and wherein the sorbent media comprises a third sorbent material which has a higher adsorption selectivity for the third gas than for the target gas.

11. The method according to claim 10 wherein the third sorbent material is an ultramicroporous material of formula $M(L^1)_2(L^2)$ having pores of an average diameter of less than 0.7 nm; wherein M is Ni, $L^1$ is pyrazine and $L^2$ is $SiF_6^{2-}$.

12. The method according to claim 1, wherein the target gas is obtained with a purity of at least 99 wt %.

13. The method according to claim 1, wherein the contacting of the gaseous composition with the sorbent media is carried out at a pressure of from 0.5 to 2 bar and a temperature of from 0° C. to 40° C.

* * * * *